US012797164B2

(12) United States Patent
Annucci

(10) Patent No.: US 12,797,164 B2
(45) Date of Patent: Nov. 17, 2026

(54) PREPARATION GUIDE FOR A DENTAL PREPARATION

(71) Applicant: EXOCAD GMBH, Darmstadt (DE)

(72) Inventor: Marco Annucci, Rome (IT)

(73) Assignee: EXOCAD GMBH, Darmstadt (DE)

(*) Notice: Subject to any disclaimer, the term of this patent is extended or adjusted under 35 U.S.C. 154(b) by 392 days.

(21) Appl. No.: 18/658,172

(22) Filed: May 8, 2024

(65) Prior Publication Data

US 2025/0345154 A1 Nov. 13, 2025

(51) Int. Cl.
*A61C 8/00* (2006.01)
*A61B 34/10* (2016.01)

(52) U.S. Cl.
CPC .............. *A61C 8/009* (2013.01); *A61B 34/10* (2016.02); *A61C 8/001* (2013.01); *A61B 2034/105* (2016.02); *A61B 2034/107* (2016.02); *A61B 2034/108* (2016.02)

(58) Field of Classification Search
CPC ..... A61C 8/009; A61C 8/001; A61C 13/0004; A61C 1/084; A61C 9/0053; A61C 1/082; A61B 34/10; A61B 2034/105; A61B 2034/107; A61B 2034/108; B22F 10/28; B22F 10/80; B33Y 50/00; G16H 50/50; G16H 20/40; G16H 30/40
See application file for complete search history.

(56) References Cited

U.S. PATENT DOCUMENTS

| | | | | |
|---|---|---|---|---|
| 7,063,532 B1 * | 6/2006 | Jones | A61C 7/00 | 433/213 |
| 2008/0014558 A1 * | 1/2008 | Matov | A61C 19/04 | 433/213 |
| 2009/0220134 A1 * | 9/2009 | Cahill | A61B 6/51 | 382/128 |
| 2023/0087800 A1 * | 3/2023 | Bielser | A61C 13/0004 | 433/24 |
| 2023/0113425 A1 * | 4/2023 | Wang | G06T 7/0012 | 433/2 |
| 2023/0419631 A1 | 12/2023 | Ezhov et al. | | |

FOREIGN PATENT DOCUMENTS

EP 2921127 B1 4/2019

* cited by examiner

*Primary Examiner* — Christopher W Carter
(74) *Attorney, Agent, or Firm* — PERRY + CURRIER INC.

(57) ABSTRACT

The invention relates to a method for generating a three-dimensional digital guide model of a physical preparation guide for a dental preparation of a patient's jaw. A three-dimensional digital jaw model and a definition of tooth positions is received. The tooth positions comprise one or more target tooth positions for one or more artificial teeth. The three-dimensional digital jaw model is overlaid with a three-dimensional digital corrugated surface. The overlaying comprises adjusting a waveform of the corrugation with local minima and maxima, such that the local minima are arranged at the positions of the teeth, while the local maxima are arranged between the positions of the teeth. The three-dimensional digital guide model is generated using the three-dimensional digital corrugated surface with the adjusted waveform.

17 Claims, 15 Drawing Sheets

PREPARATION GUIDE FOR A DENTAL PREPARATION

FIELD OF THE INVENTION

The invention relates to the field of dental technology, in particular to a method for generating a three-dimensional digital guide model of a physical preparation guide for a dental preparation of a patient's jaw.

BACKGROUND

In dentistry, there may be a need to provide a patient with one or more artificial teeth. Such artificial teeth may be used for replacing missing individual teeth in case of single tooth restorations, multiple teeth in case of multi-teeth restoration, or even to restore edentulous dental arches. Natural teeth may be exposed to normal mechanical forces, such as chewing, as well as abnormal mechanical forces, such as bruxism and traumatic injury. Furthermore, natural teeth may also be affected by disease, in particular oral disease. All this may affect teeth and, in some cases, may result in a loss of one or more teeth.

A replacement of one or more missing teeth may require a dental preparation of the patient's jaw, which is missing the teeth. Such a preparation may be challenging.

SUMMARY

It is an objective to provide for a method for generating a three-dimensional digital guide model of a physical preparation guide for a dental preparation of a patient's jaw, a computer program product for generating such a three-dimensional digital guide model, a computer device for generating such a three-dimensional digital guide model, and a manufacturing system comprising such a computer device as well as one or more manufacturing devices configured to manufacture the physical guide model.

In one aspect, the invention relates to a method for generating a three-dimensional digital guide model of a physical preparation guide for a dental preparation of a patient's jaw. The method comprises receiving a three-dimensional digital jaw model of the patient's jaw. A definition of tooth positions of a set of teeth comprising a plurality of teeth is received. The tooth positions comprise one or more target tooth positions for one or more artificial teeth comprised by the set of teeth. A three-dimensional digital corrugated surface is generated. The corrugation of the three-dimensional digital corrugated surface is defined by a waveform comprising local minima and maxima. The three-dimensional digital corrugated surface extends along a reference plane extending perpendicular to a longitudinal direction of the teeth, while the corrugation extends in the longitudinal direction.

The three-dimensional digital jaw model is overlaid with the three-dimensional digital corrugated surface. The overlaying comprises adjusting the waveform using the tooth positions, such that the local minima of the waveform are arranged at the positions of the teeth, while the local maxima of the waveform are arranged between the positions of the teeth. The three-dimensional digital guide model of the physical preparation guide is generated using the three-dimensional digital corrugated surface with the adjusted waveform and the three-dimensional digital jaw model. Data for controlling a manufacturing of the physical preparation guide is provided. The data defines the three-dimensional digital guide model as a template for the physical preparation guide.

The waveform used for generating the three-dimensional digital corrugated surface may comprise a predefined number of minima and/or maxima. The number of minima may, e.g., corresponded to the number of target tooth positions. Thus, the waveform may take into account all the artificial teeth and comprise a minimum for each of the artificial teeth. For example, the set of teeth may only comprise the artificial teeth and the tooth positions may only comprise target tooth positions of the artificial teeth. For example, in case of an edentulous jaw, only target tooth positions of artificial teeth may be taken into account. But also in case of jaw, which comprises one or more natural teeth, only target tooth positions of artificial teeth may be taken into account.

For generating the three-dimensional digital guide model, e.g., the whole three-dimensional digital corrugated surface with the adjusted waveform may be taken into account.

The artificial teeth may, e.g., be artificial teeth arranged adjacent to each other along a dental arch. Thus, the target tooth positions may be tooth positions arranged adjacent to each other along the dental arch.

The number of minima may, e.g., be larger than the number of target tooth positions. Thus, one or more tooth positions of natural teeth adjacent to the artificial teeth may be taken into account. For generating the three-dimensional digital guide model, e.g., only a section of the three-dimensional digital corrugated surface with the adjusted waveform may be taken into account, which comprises minima arranged at target tooth positions.

For example, the waveform used for generating the three-dimensional digital corrugated surface may extend along the dental arch comprising an alternating sequence of minima and maxima along the dental arch. For example, opposite endpoints of the waveform may be provided by maxima.

A difference in height between adjacent minima and maxima of the waveform may, e.g., be adjusted to corresponded to a predefined insertion depth of the artificial teeth into a jaw bone of the patient's jaw. The predefined insertion depth defines a difference in height between a bottom of a basal section of an artificial tooth, arranged within the jaw bone, and a bone crest of the jaw bone. For example, the different in height between minima and maxima may be equal for all minima and maxima comprised by the waveform. Thus, the predefined insertion depth may be equal for all artificial teeth.

The waveform may be a periodic waveform. The waveform may, e.g., be described by a sine or cosine function. The sine function may, e.g., have the form $y=a\cdot\sin(b\cdot x)$. The variable x may, e.g., describe a position within the reference plane. The variable y may describe a position in a direction perpendicular to the reference plane. The variable x may, e.g., describe a position along a dental arch of the patient. The factor a describes the amplitude of the sine function. For example, a may be chosen to correspond to half the insertion depth. The factor b describes an adjustment of the length p of the period of the sine function, which is defined by $p=|2\pi/b|$. The length p of the period may, e.g., be adjusted such that it corresponds to a distance between the position of two adjacent artificial teeth. The cosine function may, e.g., have the form $y=c\cdot\cos(d\cdot x)$. The variable x may, e.g., describe a position within the reference plane. The variable y may describe a position in a direction perpendicular to the reference plane. The variable x may, e.g., describe a position along a dental arch of the patient. The factor c describes the amplitude of the cosine function. For example, c may be chosen to correspond to half the insertion depth. The factor d describes an adjustment of the length p of the period of the cosine function, which is defined by $p=|2\pi/d|$. The length p of the period may, e.g., be adjusted such that it corresponds to a distance between the position of two adjacent artificial teeth.

The adjusting of the waveform may, e.g., comprise an adjusting of a position of the waveform within a plane extending parallel to the reference plane, which extends perpendicular to the longitudinal direction of the teeth. For example, the waveform may be moved along a dental arch. The position of the waveform may be adjusted, such that the local minima of the waveform are arranged at the positions of the teeth, while the local maxima of the waveform are arranged between the positions of the teeth.

The adjusting of the waveform may, e.g., comprise an adjusting of a position of the waveform in a direction perpendicular to the reference plane. For example, the position of the waveform in the direction perpendicular to the reference plane may be adjusted such that the maxima of the waveform are arranged on the level as bone crest of the jaw bone, i.e., a current bone crest of the jaw bone or a bone crest of the jawbone to be achieved by a bone reconstruction.

The adjusting of the waveform may, e.g., comprise an adjusting of an amplitude of the waveform. For example, the amplitude of the waveform may be adjusted such that it corresponds to a predefined insertion depth of the artificial teeth into a jaw bone of the patient's jaw. The adjusting of the waveform may, e.g., comprise an adjusting of a length of a period of the waveform. The length of the period may, e.g., be adjusted such that it corresponds to a distance between the position of two adjacent artificial teeth.

The generating of the three-dimensional digital corrugated surface may, e.g., comprise an extending of the waveform, which may be defined by a corrugated line, in a direction parallel to the reference plane, such that the resulting corrugated surface extends along the reference plane. The corrugation defined by the waveform may extend in a direction parallel to the longitudinal direction of the teeth, e.g., the artificial and/or natural teeth. Thus, the corrugation of the resulting corrugated surface may also extend in the direction parallel to the longitudinal direction of the teeth.

Using a three-dimensional digital corrugated surface for defining tissue to be remove, e.g., for providing space for basal sections of the artificial teeth, may have the beneficial effect that an amount of tissue being removed may be minimized. Using the corrugated surface, the form of the preparation may efficiently be adjusted to the basal sections of the artificial teeth. Thus, aesthetics in form of the artificial teeth may be realized without destroying any more tissue than necessary, so that the natural hard and soft tissue of the patient, e.g., the jawbone and gingiva, may be preserved as far as possible. By preserving the hard and soft tissue, natural aesthetics of the patient may be preserved. In addition, the more natural tissue is preserved, the better potential future degeneration or damage of the remaining tissue may be prevented.

In particular, a contour line defined by the waveform of the three-dimensional digital corrugated surface may have similar aesthetics as a natural gingiva contour line. On the other hand, the three-dimensional digital corrugated surface is a comparatively simple geometric shape, which is easy to be defined, adjusted and implemented by the preparation.

For example, the jawbone may be preserved as far as possible. By preserving the jawbone, in particular also the gingiva may be preserved. Otherwise, without a sufficient portion of the jawbone, the gingiva may not be sufficiently supported and therefore slowly and inexorably recede. Thus, using the three-dimensional digital corrugated surface a bone preparation may be enabled, which prepares and protects the hard and soft tissue with a natural aesthetic.

The three-dimensional digital corrugated surface may, e.g., be provided in form of a mesh, e.g., a polygon mesh. The polygon mesh may be provided by a collection of vertices, edges, and faces that defines the shape of a surface a polyhedral object.

A preparation guide refers to a template configured to be arranged in a patient's mouth, e.g., on a mandible or maxilla. It defines, e.g., a position and/or a contour of a preparation of the patient's tissue. The preparation guide may, e.g., be a bone reduction guide defining a contour of a bone reduction, a bone reconstruction guide defining a contour of a bone reconstruction, a gingiva shaping guide defining a contour of a gingiva, or a drilling guide defining positions of holes to be drilled into the bone, e.g., for implants. A bone reduction guide defines a contour of a patient's bone to be achieved by a bone reduction, e.g., by a removal of bone tissue.

A bone reconstruction guide defines a contour of a patient's bone to be achieved by a bone reconstruction, i.e., by a regeneration or adding of missing bone. A bone reconstruction may, e.g., be used to fill holes in the bone resulting from tooth extractions, to fill bone defects caused by disease, like dental infection of abscess or periodontal disease, and/or to extend a section of the bone with an insufficient amount of bone tissue for firmly holding an implant. For example, people who have been edentulous for a prolonged period may not have enough bone left for implants in necessary locations. Also, a trauma or the natural process of aging may result in a loss of bone tissue.

For a bone reconstruction, e.g., bone grafts, guided bone regeneration, or elevation of the maxillary sinus may be used.

Bone grafts may, e.g., be used to provide a structure for the bone tissue to regenerate around. Bone tissue has the ability to regenerate completely if provided the space into which to grow. As native bone grows, it may replace the graft material, resulting in a fully integrated region of new bone. The biologic mechanisms that provide a rationale for bone grafting are osteoconduction, osteoinduction and osteogenesis. Different forms of bone grafts may be used, such as autograft bone tissue, i.e., bone obtained from the same individual receiving the graft; allograft bone tissue, i.e., bone harvested from an individual other than the one receiving the graft; xenograft bone tissue, i.e., animal bone tissue, e.g., from bovine sources such as cows or pigs, which has been sterilized and processed for safe implantation into human tissue; or alloplastic materials. Bone grafts may, e.g., be used prior to an implant placement or simultaneously.

Guided bone regeneration uses a barrier membrane to direct a growth of new bone issue at a site with insufficient volume or dimension of bone. Guided bone regeneration, e.g., refers to ridge augmentation or bone regenerative procedures.

Maxillary sinus floor augmentation, also referred to as sinus lift, aims to increase the amount of bone in the posterior maxilla, e.g., in the area of the premolar and molar teeth, by lifting the lower sinus membrane and placing a bone graft.

A gingiva shaping guide defines a contour of a patient's gingiva, to be achieved by a gingiva reduction, e.g., by a removal of gingiva tissue. For a reduction of gingiva tissue, e.g., laser shaping may be used.

A drilling guide defines positions of holes to be drilled into the jawbone, e.g., for inserting implants for fastening a restoration, like a dental bridge, to the patient's jaw. In addition to defining the position of the holes, the drilling guide may, e.g., provide a guidance for a drilling tool. It may, e.g., also define a depth up to which the drilling tool is to be inserted into the drilling guide, thereby restricting the depths of the holes being drilled.

The preparation guide may, e.g., be configured to be used for preparing a patient's mandible or maxilla for receiving one or more implant supported restorations. The restoration may, e.g., comprise an implant supported artificial tooth in form of a crown. The implant supported tooth may comprise an abutment, which is to be received by the implant and fastened to the implant, e.g., using a screw.

The preparation guide may, e.g., be configured to be used for preparing a patient's mandible or maxilla for receiving an implant supported set of artificial teeth, also referred to as a dental bridge. The implant supported set of artificial teeth may comprise abutments, which are configured to be received by the implants and fastened to the implants, e.g., using screws. The implant supported set of artificial teeth is, e.g., an implant supported dental bridge. The implant supported set of artificial teeth is, e.g., an implant supported complete dental arch. An implant supported complete dental arch is a complete dental arch of artificial teeth configured to be fastened to implants inserted into a patient's toothless jaw.

For preparing a patient's mandible or maxilla for receiving an implant supported set of artificial teeth, e.g., a set of preparation guides with a plurality of preparation guides may be provided for successively preparing the patient's mandible or maxilla. Such a set of preparation guides may, e.g., comprise a bone reduction guide, a gingiva shaping guide, and/or a drilling guide. Such a set of preparation guides may, e.g., comprise a bone reconstruction guide, and/or a drilling guide.

The three-dimensional digital jaw model of the patient's jaw may, e.g., comprise a dimensional digital jawbone model of a jawbone comprised by the patient's jaw. The three-dimensional digital jawbone model may, e.g., be generated using scan data of the patient's jawbone.

The three-dimensional digital jaw model of the patient's jaw may, e.g., comprise a dimensional digital gingiva model of a gingiva comprised by the patient's jaw. The three-dimensional digital gingiva model may, e.g., be generated using scan data of the patient's gingiva.

The three-dimensional digital jaw model of the patient's jaw may, e.g., comprise one or more three-dimensional digital tooth models of natural teeth comprised by the patient's jaw. The three-dimensional digital tooth models may, e.g., be generated using scan data of the patient's natural teeth.

The scan data of the patient's jaw may comprise, e.g., CT scan data and/or CBCT scan data. The CT scan data and/or CBCT scan data may, e.g., provide information about the structure of the patient's jawbone and/or teeth. The scan data of the patient's jaw may comprise, e.g., optical scan data. The optical scan data may, e.g., comprise intraoral optical scan data or optical scan data from a scan of a classical mold/impression. The optical scan data may, e.g., provide information about the surface structure of the patient's intraoral tissue comprising teeth and the gingiva.

The positions of teeth may comprise positions of one or more natural teeth of the patient. For example, the three-dimensional digital jaw model may comprise one or more three-dimensional digital tooth models of natural teeth. Thus, the three-dimensional digital jaw model may provide the definition of the positions of the natural teeth. The position information may, e.g., origin from scan data of the patient's natural teeth.

For example, the definition of the position of the natural teeth may be provided in addition to the three-dimensional digital jaw model.

The definition of tooth positions of the set of teeth may comprise one or more target tooth positions for one or more artificial teeth comprised by the set of teeth. For example, the definition of the one or more target tooth positions may be provided in addition to the three-dimensional digital jaw model. For example, the positions may be provided in form of coordinates defining the target tooth positions within the three-dimensional digital jaw model. For example, one or more three-dimensional digital tooth models of artificial teeth may be provided, which are arranged at the target tooth positions within the three-dimensional digital jaw model.

For example, the minima are formed by first straight lines of a first constant height extending in oral direction parallel to the reference plane through the target positions of the teeth. For example, the maxima are formed by second straight lines of a second constant height extending in oral direction parallel to the reference plane between the target positions of the teeth.

For example, the waveform may be adjusted using the tooth positions, such that the local minima of the waveform are arranged at the positions of the teeth. The waveform may be provided in form of a line, which is extended parallel to the reference plane. The waveform may be extended in oral and/or vestibular direction. By extending the waveform, the minima may be extended to first straight lines of a first constant height extending in oral direction parallel to the reference plane through the target positions of the teeth.

For example, the waveform may be adjusted using the tooth positions, such that the local maxima of the waveform are arranged between the positions of the teeth. The waveform may be provided in form of a line, which is extended parallel to the reference plane. The waveform may be extended in oral and/or vestibular direction. By extending the waveform, the maxima may be extended to second straight lines of a second constant height extending in oral direction parallel to the reference plane between the target positions of the teeth.

For example, the overlaying comprises a graphically overlaying of the three-dimensional digital jaw model with the three-dimensional digital corrugated surface. A graphical overlaying may intuitively visualize, which section of the patient's jaw represented by the three-dimensional digital jaw model may have to be removed, e.g. using a bone reduction and/or gingiva shaping, and/or where additional sections may have to be added to the of the patient's jaw, e.g., using a bone reconstruction.

For example, the three-dimensional digital guide model has a form of a splint being configured to be arranged on a jaw structure defined by the received three-dimensional digital jaw model with an inner surface of the splint being defined as a negative of an outer surface of the jaw structure.

The splint as a negative of an outer surface of the jaw structure may be configured to be arranged on the respective jaw structure in a predefined position. The generating of a three-dimensional digital model of the splint may, e.g., comprise using the outer surface of the jaw structure as an inner surface of the splint and adding a predefined thickness of the splint thereon.

The jaw structure may, e.g., comprise a jawbone of the patient defined by the received three-dimensional digital jaw model. The jaw structure may, e.g., comprise one or more natural teeth and/or a gingiva of the patient defined by the received three-dimensional digital jaw model.

For example, the physical preparation guide defines a target contour line of the dental preparation. The splint comprises a cutout in an occlusal section of the splint with a contour line of the cutout being defined by an intersection line, which is defined by the intersection of the three-dimensional digital jaw model overlaid with the three-dimensional digital corrugated surface with the adjusted waveform.

The contour line of the cutout may define the target contour line of the dental preparation. Thus, the physical preparation guide may be configured to indicate, when being arranged on the jaw structure to be prepared, the target contour line to be achieved by the preparation. The achieving of the target contour line may, e.g., comprise a removal of tissue from the jaw structure, where the jaw structure extends through the cutout and beyond the contour line of the cutout. The achieving of the target contour line may, e.g., comprise a reconstruction of tissue of the jaw structure, where the jaw structure does not reach the contour line of the cutout.

For example, the jaw structure defined by the received three-dimensional digital jaw model represents a jawbone of the patient to be prepared. The three-dimensional digital jaw model representing the jawbone may, e.g., be used for generating a three-dimensional digital guide model of a bone reduction or bone reconstruction guide. Also, a three-dimensional digital jaw model representing the jawbone may, e.g., be used for generating a three-dimensional digital guide model of a drilling guide.

For example, the physical preparation guide is a bone reduction guide. The target contour line is a contour line of an occlusal surface of a jawbone of the patient to be achieved by the dental preparation comprising a bone reduction.

For example, the bone reduction comprises removing bone material from the jawbone. The jawbone may, e.g., be defined by the three-dimensional digital jaw model, from which the three-dimensional digital corrugated surface is subtracted. When overlaying the three-dimensional digital jaw model with the three-dimensional digital corrugated surface, the three-dimensional digital corrugated surface may intersect with the jawbone defined by the three-dimensional digital jaw model. For subtracting the three-dimensional digital corrugated surface waveform from the three-dimensional digital jaw model, i.e., the jawbone, the three-dimensional digital jaw model may be overlaid with the three-dimensional digital corrugated surface and all the bone material extending in occlusal direction beyond the three-dimensional digital corrugated surface waveform may be identified as bone material to be removed.

A bone reduction guide is a template configured to be arranged in a patient's mouth on a jawbone, e.g., mandible or maxilla, and defining a target contour line of the jawbone to be achieved by a bone reduction, e.g., by milling sections of the jawbone away.

For example, the physical preparation guide is a bone reconstruction guide. The target contour line is a contour line of an occlusal surface of a jawbone of the patient to be achieved by the dental preparation comprising a bone reconstruction.

For example, the bone reconstruction comprises adding reconstruction material to the jawbone. The jawbone may, e.g., be defined by the three-dimensional digital jaw model, to which a bone section is added with a contour line of an occlusal surface of the jawbone to be achieved by the reconstruction being defined by a projection of a contour of the jawbone in occlusal direction onto the three-dimensional digital corrugated surface waveform. When overlaying the three-dimensional digital jaw model with the three-dimensional digital corrugated surface, the three-dimensional digital corrugated surface may be arranged spaced apart in occlusal direction from the jawbone defined by the three-dimensional digital jaw model.

A bone reconstruction guide is a template configured to be arranged in a patient's mouth on a jawbone, e.g., mandible or maxilla, and defining a target contour line of the jawbone to be achieved by a bone reconstruction, e.g., by adding build-up structures to the jawbone.

For example, the three-dimensional digital jaw model comprises scan data of the jawbone of the patient.

For example, the scan data comprises one or more of the following: CBCT scan data, CT scan data.

CT scan data is acquired using a CT scan, i.e., a computer tomography scan. A CT scan provides computer-processed combinations of multiple X-ray measurements taken from different angles to produce tomographic, i.e., cross-sectional images. For example, a focal plane tomography may be used with images of multiple planes being taken to generate a composite panoramic image.

CBCT scan data is acquired using cone-beam computed tomography (CBCT), also referred to as digital volume tomography (DVT), may be used. CBCT consisting of X-ray computed tomography with divergent X-rays forming a cone.

For example, the jaw structure defined by the received three-dimensional digital jaw model is a gingiva of the patient to be prepared. The physical preparation guide is a gingiva shaping guide. The target contour line is an occlusal contour line of the gingiva of the patient to be achieved by the dental preparation comprising a shaping of the gingiva of the patient.

For example, the shaping of the gingiva comprises removing gingiva material from the gingiva. The received three-dimensional digital jaw model is a gingiva of the patient to be prepared. For example, leftover gingiva sections, which remain after a bone deduction, may be removed. When overlaying the three-dimensional digital jaw model, i.e., the gingiva defined by the three-dimensional digital jaw model, with the three-dimensional digital corrugated surface, the three-dimensional digital corrugated surface may intersect with the gingiva. For subtracting the three-dimensional digital corrugated surface waveform from the three-dimensional digital jaw model, i.e., the gingiva, the three-dimensional digital jaw model may be overlaid with the three-dimensional digital corrugated surface and all the gingiva material extending in occlusal direction beyond the three-dimensional digital corrugated surface waveform may be identified as gingiva material to be removed.

The preparation guide as a gingiva shaping guide may define a contour line of the gingiva to be achieved by a gingiva preparation, e.g., using a laser. A gingiva reduction guide is a template configured to be arranged in a patient's mouth on a gingiva, e.g., mandibular gingiva or maxillary gingiva, and defining a target contour line of the gingiva to be achieved by a gingiva preparation, e.g., by laser shaping the gingiva.

A preparation guide may, e.g., be made from plastic and/or metal. In case the preparation guide is intended to be used with a laser, it may, e.g., be made from metal.

For example, the three-dimensional digital jaw model comprises optical scan data of the gingiva of the patient. The optical scan data may, e.g., comprise intraoral optical scan data or optical scan data from a scan of a classical mold/impression. The optical scan data may, e.g., provide information about the surface structure of the patient's intraoral tissue comprising the gingiva to be shaped.

For example, the physical preparation guide is a drilling guide comprising first through holes defining positions of drilling holes to be drilled into the jawbone of the patient for implants.

The occlusal section of the splint has an inner surface being defined as a negative of the three-dimensional digital corrugated surface with the adjusted waveform.

The method further comprises receiving definitions of the positions of the drilling holes. The generating of the three-dimensional digital guide model comprises defining the first through holes using the definitions of the positions of the drilling holes.

The drilling guide may, e.g., define positions of holes to be drilled into the jawbone for implants, in order to fix a prothesis to the jawbone. An occlusal section of the splint, i.e., the drilling guide, may have an inner surface being defined as a negative of the three-dimensional digital corrugated surface with the adjusted waveform. For example, a bone reduction guide or a bone reconstruction guide may be used to prepare the jawbone resulting in an occlusal surface of the jawbone, which corresponds to the three-dimensional digital corrugated surface. Thus, a splint with an inner surface being defined as a negative of the three-dimensional digital corrugated surface with the adjusted waveform may tightly fit onto the prepared jawbone enabling a precise definition of the drilling holes.

The corrugated form may not only provide support for the drilling guide in a direction towards the maxilla in case of the maxilla or a direction towards the mandible in case of the mandible, but also in lateral direction. Thus, the shape achieved by a bone reduction using the aforementioned bone reduction guide may further improve the stability of the drilling guide on the jawbone, e.g., the maxilla or mandible.

For example, the three-dimensional digital jaw model comprises scan data of the jawbone of the patient. For example, the scan data comprises one or more of the following: CBCT scan data, CT scan data.

The CBCT scan data and/or CT scan data may provide inside into internal structures of the jawbone, enabling a determining of positions for the implants within the jawbone, which provide sufficient support for the implant, and/or where the implants do not interfere with sensitive tissue structures within the jawbone, like nerves and/or blood vessels.

For example, the method further comprises defining positions of one or more second through holes to be comprised by the three-dimensional digital guide model. The second through holes are configured for receiving fastening means for fastening the physical guide model to the patient's jaw. The definitions of the positions of the second through holes are used for the generating of the three-dimensional digital guide model comprising the one or more second through holes.

For defining the positions of the second through holes, e.g., CBCT scan data and/or CT scan data may be used. For example, the three-dimensional digital jaw model comprises CBCT scan data and/or CT scan data of the jawbone of the patient. The CBCT scan data and/or CT scan data may provide inside into internal structures of the jawbone, enabling a determining of positions for the fastening means within the jawbone, which provide sufficient support for the fastening means, where the fastening means do not interfere with other elements to be inserted into the jawbone, like implants, and/or where the fastening means do not interfere with sensitive tissue structures within the jawbone, like nerves and/or blood vessels.

For example, all teeth comprised by the set of teeth are artificial teeth. All tooth positions received are target positions of the artificial teeth of the set of teeth.

For example, the set of teeth comprises a full dental arch of artificial teeth.

For example, the jaw is a mandible or a maxilla of the patient.

For example, the method further comprises manufacturing of the physical preparation guide using the data provided for controlling the manufacturing with the manufactured physical preparation guide being a physical copy of the template defined by the provided data.

For the manufacturing of the physical preparation guide, e.g., computer-controlled additive and/or subtractive methods may be used. For example, the physical preparation guide may be manufactured using one of the following: machining, 3D printing, casting.

Examples may have the beneficial effect, that the physical preparation guide may be manufactured using a machining device configured to manufacture the physical preparation guide by processing a blank. For example, the physical preparation guide may be manufactured using a 3D printing device, i.e., a printer, configured to print the respective physical preparation guide. For example, a computer-controlled additive and/or subtractive method may be used for manufacturing a casting matrix configured for casting the physical preparation guide by inserting casting material into the casting matrix and curing the inserted casting material.

For example, the manufactured physical preparation guide is one of the following: a bone reduction guide, a bone reconstruction guide, a gingiva shaping guide, or a drilling guide.

The physical preparation guide may be configured to be used for preparing a patient's jaw for receiving a restoration. The restoration may, e.g., be an implant supported crown. An implant supported crown, also referred to as a dental implant crown, may be connected to an implant using an abutment, also referred to as a connector, and a fastening means, like a screw. Alternatively, the crown may, e.g., be bonded to the abutment using bonding material.

The restoration may, e.g., be an implant supported bridge. A bridge is a dental restoration element in form of a permanent appliance used to replace one or more missing teeth. A dental bridge comprises a plurality of artificial dental elements that are fused together, e.g., one or more artificial teeth are definitively joined to adjacent teeth. It may be connected to implants using abutments, also referred to as connectors, and a fastening means, like screws. Alternatively, the bridge may, e.g., be bonded to the abutments using bonding material.

In another aspect, the invention relates to a computer program product for generating a three-dimensional digital guide model of a physical preparation guide for a dental preparation of a patient's jaw. The computer program product comprises a non-transitory computer readable storage medium having program instructions embodied therewith. The program instructions are executable by a processor of a computer device to cause the computer device to receive a three-dimensional digital jaw model of the patient's jaw. Further, a definition of tooth positions of a set of teeth comprising a plurality of teeth is received. The tooth positions comprise one or more target tooth positions for one or more artificial teeth comprised by the set of teeth. A three-dimensional digital corrugated surface is generated. The corrugation of the three-dimensional digital corrugated surface is defined by a waveform comprising local minima and maxima. The three-dimensional digital corrugated surface extends along a reference plane extending perpendicular to a longitudinal direction of the teeth, while the corrugation extends in the longitudinal direction.

The three-dimensional digital jaw model is overlaid with the three-dimensional digital corrugated surface. The overlaying comprises adjusting the waveform using the tooth positions, such that the local minima of the waveform are arranged at the positions of the teeth, while the local maxima of the waveform are arranged between the positions of the teeth. The three-dimensional digital guide model of the physical preparation guide is generated using the three-dimensional digital corrugated surface with the adjusted waveform and the three-dimensional digital jaw model. Data for controlling a manufacturing of the physical preparation guide is provided. The data defines the three-dimensional digital guide model as a template for the physical preparation guide.

The program instructions provided by the computer program product may, e.g., be executable by the processor of the computer device to cause the computer device to execute any of the aforementioned examples of the method for generating a three-dimensional digital guide model.

For example, the generated three-dimensional digital guide model is a three-dimensional digital model one of the following: a bone reduction guide, a bone reconstruction guide, a gingiva shaping guide, or a drilling guide.

In another aspect, the invention relates to a computer program for generating a three-dimensional digital guide model of a physical preparation guide for a dental preparation of a patient's jaw. The computer program comprises program instructions. The program instructions are executable by a processor of a computer device to cause the computer device to receive a three-dimensional digital jaw model of the patient's jaw. Further, a definition of tooth positions of a set of teeth comprising a plurality of teeth is received. The tooth positions comprise one or more target tooth positions for one or more artificial teeth comprised by the set of teeth. A three-dimensional digital corrugated surface is generated. The corrugation of the three-dimensional digital corrugated surface is defined by a waveform comprising local minima and maxima. The three-dimensional digital corrugated surface extends along a reference plane extending perpendicular to a longitudinal direction of the teeth, while the corrugation extends in the longitudinal direction.

The three-dimensional digital jaw model is overlaid with the three-dimensional digital corrugated surface. The overlaying comprises adjusting the waveform using the tooth positions, such that the local minima of the waveform are arranged at the positions of the teeth, while the local maxima of the waveform are arranged between the positions of the teeth. The three-dimensional digital guide model of the physical preparation guide is generated using the three-dimensional digital corrugated surface with the adjusted waveform and the three-dimensional digital jaw model. Data for controlling a manufacturing of the physical preparation guide is provided. The data defines the three-dimensional digital guide model as a template for the physical preparation guide.

The program instructions provided by the computer program may, e.g., be executable by the processor of the computer device to cause the computer device to execute any of the aforementioned examples of the method for generating a three-dimensional digital guide model.

For example, the generated three-dimensional digital guide model is a three-dimensional digital model one of the following: a bone reduction guide, a bone reconstruction guide, a gingiva shaping guide, or a drilling guide.

In another aspect, the invention relates to a computer device for generating a three-dimensional digital guide model of a physical preparation guide for a dental preparation of a patient's jaw. The computer device comprises a processor and a memory storing program instructions executable by the processor. Execution of the program instructions by the processor causes the computer device to receive a three-dimensional digital jaw model of the patient's jaw. Further, a definition of tooth positions of a set of teeth comprising a plurality of teeth is received. The tooth positions comprise one or more target tooth positions for one or more artificial teeth comprised by the set of teeth. A three-dimensional digital corrugated surface is generated. The corrugation of the three-dimensional digital corrugated surface is defined by a waveform comprising local minima and maxima. The three-dimensional digital corrugated surface extends along a reference plane extending perpendicular to a longitudinal direction of the teeth, while the corrugation extends in the longitudinal direction.

The three-dimensional digital jaw model is overlaid with the three-dimensional digital corrugated surface. The overlaying comprises adjusting the waveform using the tooth positions, such that the local minima of the waveform are arranged at the positions of the teeth, while the local maxima of the waveform are arranged between the positions of the teeth. The three-dimensional digital guide model of the physical preparation guide is generated using the three-dimensional digital corrugated surface with the adjusted waveform and the three-dimensional digital jaw model. Data for controlling a manufacturing of the physical preparation guide is provided. The data defines the three-dimensional digital guide model as a template for the physical preparation guide.

Execution of the program instructions by the processor of the computer device may, e.g., cause the computer device to execute any of the aforementioned examples of the aforementioned examples of the method for generating a three-dimensional digital guide model.

For example, the generated three-dimensional digital guide model is a three-dimensional digital model one of the following: a bone reduction guide, a bone reconstruction guide, a gingiva shaping guide, or a drilling guide.

In another aspect, the invention relates to a manufacturing system comprising the computer device of any of the aforementioned examples of a computer device. The manufacturing system further comprises one or more manufacturing devices configured to manufacture the physical guide model. Execution of the program instructions by the processor further causes the computer device to control the one or more manufacturing devices to manufacture the physical guide model using the data provided for controlling the manufacturing with the manufactured physical preparation guide being a physical copy of the template defined by the data provided.

Execution of the program instructions by the processor of the computer device may, e.g., cause the computer device to control the one or more manufacturing devices of the manufacturing system to manufacture any of the aforementioned examples of the manufactured physical preparation guide.

For example, the manufactured physical preparation guide is one of the following: a bone reduction guide, a bone reconstruction guide, a gingiva shaping guide, or a drilling guide.

For the manufacturing of the physical preparation guide, e.g., computer-controlled additive and/or subtractive methods may be used. For example, the physical preparation guide may be manufactured using one of the following: machining, 3D printing, casting.

For example, the one or more manufacturing devices of the manufacturing system may comprise one or more of the following: a machining device, a 3D printing device.

Examples may have the beneficial effect, that the physical preparation guide may be manufactured using a machining device configured to manufacture the physical preparation guide by processing a blank. For example, the physical preparation guide may be manufactured using a 3D printing device, i.e., a printer, configured to print the respective physical preparation guide. For example, a computer-controlled additive and/or subtractive method may be used for manufacturing a casting matrix configured for casting the physical preparation guide by inserting casting material into the casting matrix and curing the inserted casting material.

The above-described examples and embodiments may be combined freely as long as the combinations are not mutually exclusive.

BRIEF DESCRIPTION OF THE DRAWINGS

In the following, examples are described in greater detail making reference to the drawings in which.

DETAILED DESCRIPTION

Figure 1:
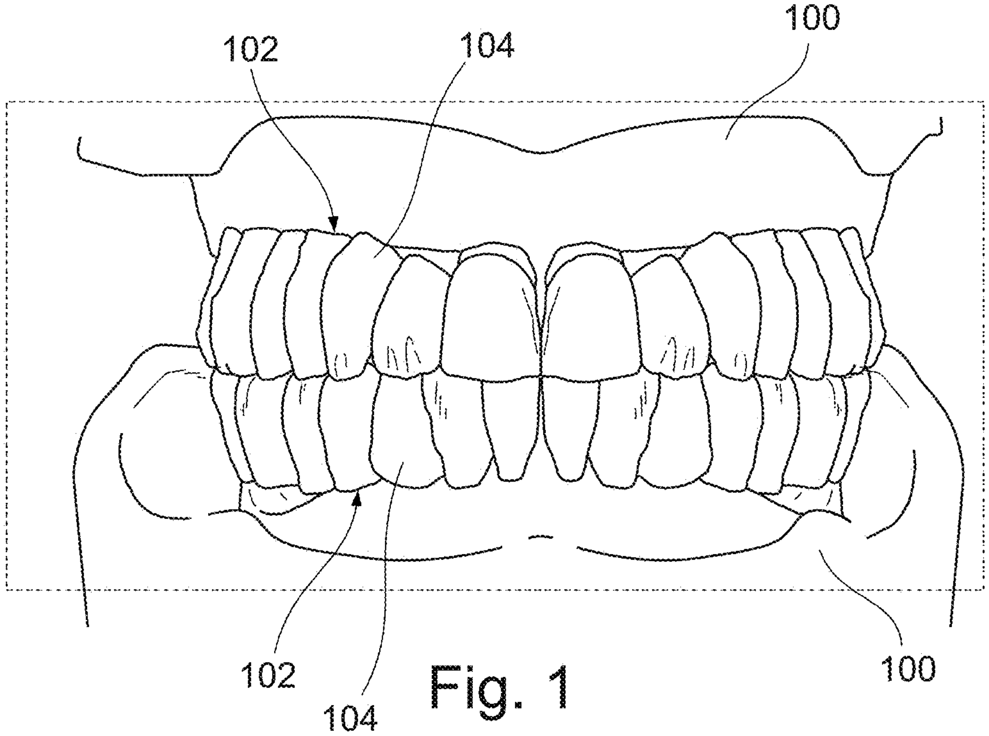
FIG. 1 shows exemplary three-dimensional digital jaw models.

In the following, similar elements are denoted by the same reference numerals. Elements which have been discussed previously will not necessarily be discussed in later figures if the function is equivalent.

FIG. 1 shows two exemplary three-dimensional digital jaw models 100 of a patient's jaws. In case of FIG. 1, a three-dimensional digital jaw model 100 of a patient's mandible and a three-dimensional digital jaw model 100 of a patient's maxilla are shown, i.e., a mandibular and a maxillary model. Further, positions 102 of teeth relative to the three-dimensional digital jaw models 100 are defined. Positions 102 are defined for mandibular teeth relative to the three-dimensional digital jaw model 100 of a patient's mandible. Further, positions 102 are defined for maxillary teeth relative to the three-dimensional digital jaw model 100 of a patient's maxilla.

In FIG. 1, the positions 102 of the teeth are defined by three-dimensional digital tooth models 104 arranged at the respective positions 102. In case of FIG. 1, the three-dimensional digital tooth models 104 comprise three-dimensional digital tooth models 104 of mandibular and maxillary teeth. Alternatively, the positions 102 of the teeth could also be indicated by other geometrical indicators. The teeth may e.g., be artificial teeth and the positions 102 of the teeth target positions for the teeth. Thus, the three-dimensional digital tooth models 104 shown in FIG. 1 may, e.g., be tooth models of artificial teeth arranged at the target positions 102.

Figure 2:
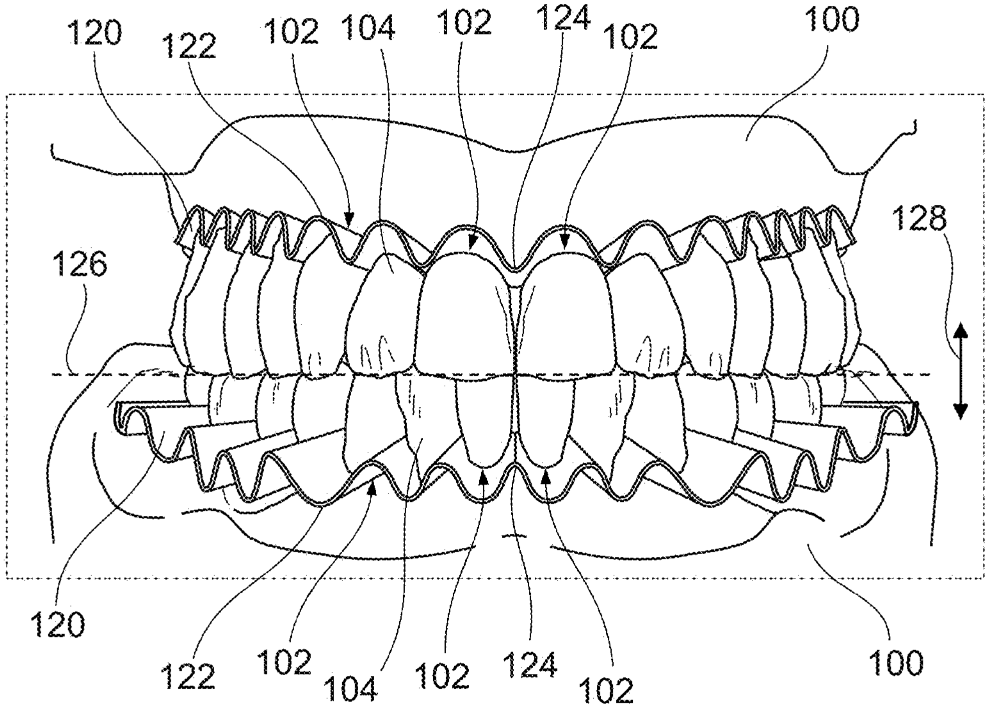
FIG. 2 shows exemplary three-dimensional digital jaw models overlaid with three-dimensional digital corrugated surfaces.

FIG. 2 shows the exemplary three-dimensional digital jaw models 100 of FIG. 1, each of which is overlaid with a three-dimensional digital corrugated surface 120. The three-dimensional digital jaw model 100 of a patient's mandible is overlaid with a three-dimensional digital corrugated surface 120 and the three-dimensional digital jaw model 100 of a patient's maxilla is overlaid with a three-dimensional digital corrugated surface 120.

The corrugations of the three-dimensional digital corrugated surfaces 120 are each defined by a waveform comprising local minima 122 and maxima 124. Each of the three-dimensional digital corrugated surfaces 120 extends along a reference plane 126 extending perpendicular to a longitudinal direction 128 of the teeth of the respective jaw. The longitudinal direction 128 may, e.g., be an averaged direction. It may, e.g., be a direction of properly arranged artificial teeth, i.e., a target direction of the artificial teeth.

The longitudinal direction 128 may, e.g., be a direction perpendicular to an occlusal plane. In this case, the reference plane 126 may be provided by the occlusal plane.

The corrugations of the three-dimensional digital corrugated surfaces 120 extend in the longitudinal direction 128. The overlaid three-dimensional digital corrugated surfaces 120 are each adjusted, such that the local minima 122 are arranged at the positions of the teeth and the local maxima 124 are arranged between the positions 102 of the teeth.

Figure 3:
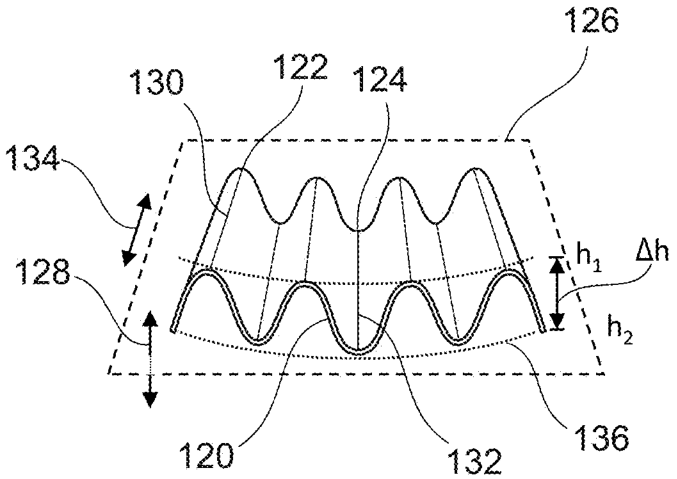
FIG. 3 shows an exemplary three-dimensional digital corrugated surface.

FIG. 3 shows an exemplary three-dimensional digital corrugated surface 120. The corrugation of the three-dimensional digital corrugated surface 120 is defined by a waveform comprising local minima 122 and local maxima 124. The three-dimensional digital corrugated surface 120 extends along a reference plane 126. This reference plane 126 extends perpendicular to a longitudinal direction 128 of the teeth. Corrugation, i.e., the local minima 122 and local maxima 124 extend in the longitudinal direction 128.

The local minima 122 are formed by first straight lines 130 of a first constant height $h_1$. The first straight lines 130 extend in oral direction 134 parallel to the reference plane 126 through the target positions 102 of the teeth. The local maxima 124 are formed by second straight lines 132 of a second constant height $h_2$. The difference in height between the second constant height $h_1$ and the first constant height $h_1$ is $\Delta h$. The second straight lines 132 extend in oral direction 134 parallel to the reference plane 126 between the target positions 102 of the teeth. The first and second straight lines 130, 132, when extending in oral direction, may, e.g., be arranged perpendicular to the tooth arch indicated in FIG. 3 by dotted line 136.

Figure 4:
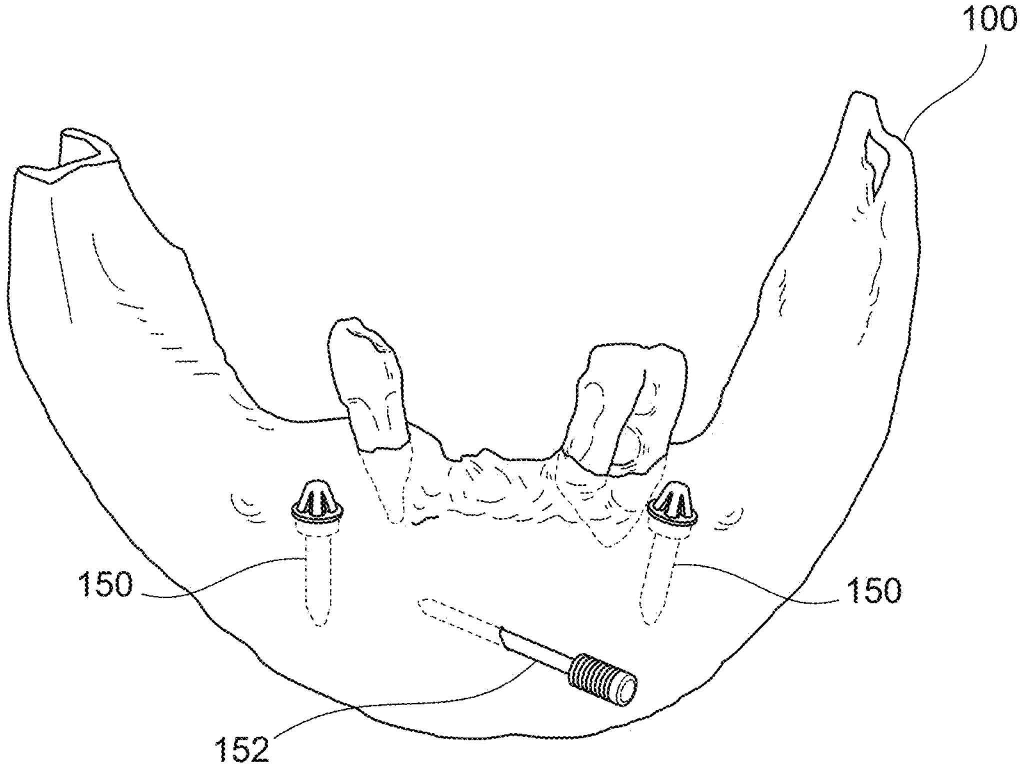
FIG. 4 shows an exemplary three-dimensional digital jaw model.

FIG. 4 shows an exemplary three-dimensional digital jaw model 100 is shown. The three-dimensional digital jaw model 100 shown in FIG. 4 is a model of a patient's mandible, i.e., lower jaw bone, which comprises also natural teeth of the patient. The three-dimensional digital jaw model 100 may, e.g., comprises scan data the mandible with the teeth. The scan data may, e.g., comprise CBCT scan data and/or CT scan data. The natural teeth of the patient comprised by the three-dimensional digital jaw model 100 are to be replaced and supplemented by artificial teeth. For example, an implant-supported bridge is to be added to the patient's mandible represented by the three-dimensional digital jaw model 100. The three-dimensional digital jaw model 100 may be used for planning positions of the implants 150 to arranged within the patient's mandible for fixing the implant-supported bridge to the mandible. Further, a position of a fastening means 152, e.g., a screw, for fastening a physical preparation guide to the mandible may be planned using the three-dimensional digital jaw model 100.

Figure 5:
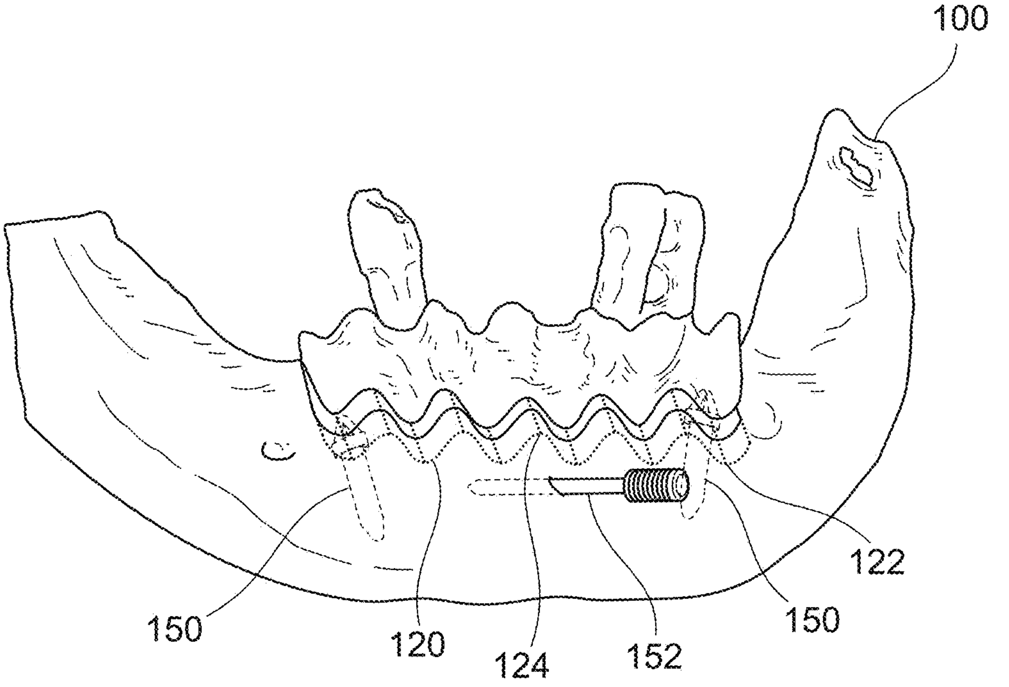
FIG. 5 shows the exemplary three-dimensional digital jaw model of FIG. 4 with a three-dimensional digital corrugated surface.

FIG. 5 shows the exemplary three-dimensional digital jaw model 100 of FIG. 4 with a three-dimensional digital corrugated surface 120 indicated by dotted lines. The corrugation of the three-dimensional digital corrugated surface 120 is defined by a waveform comprising local minima 122 and local maxima 124. The three-dimensional digital jaw model 100 is overlaid with the three-dimensional digital corrugated surface 120. The three-dimensional digital corrugated surface 120 defines a cutting surface for cutting off a section of the three-dimensional digital jaw model 100 comprising the natural teeth to be replaced by the implant-supported bridge with a plurality of teeth. The three-dimensional digital corrugated surface 120 comprises six local minima 122. The positions of the six local minima 122 are defined by six target positions of six artificial teeth to be comprised by the implant-supported bridge. Indicated by dashed lines are the planned positions of the implants 150. Furthermore, the planned position of the fastening means 152 for fastening a physical preparation guide to the mandible is shown.

The planned positions of the implants 150 are arranged within the intersection of the three-dimensional digital corrugated surface 120 with the three-dimensional digital jaw model 100. The planned position of the fastening means 152 is arranged in apical direction below the intersection of the three-dimensional digital corrugated surface 120 with the three-dimensional digital jaw model 100.

Figure 6:
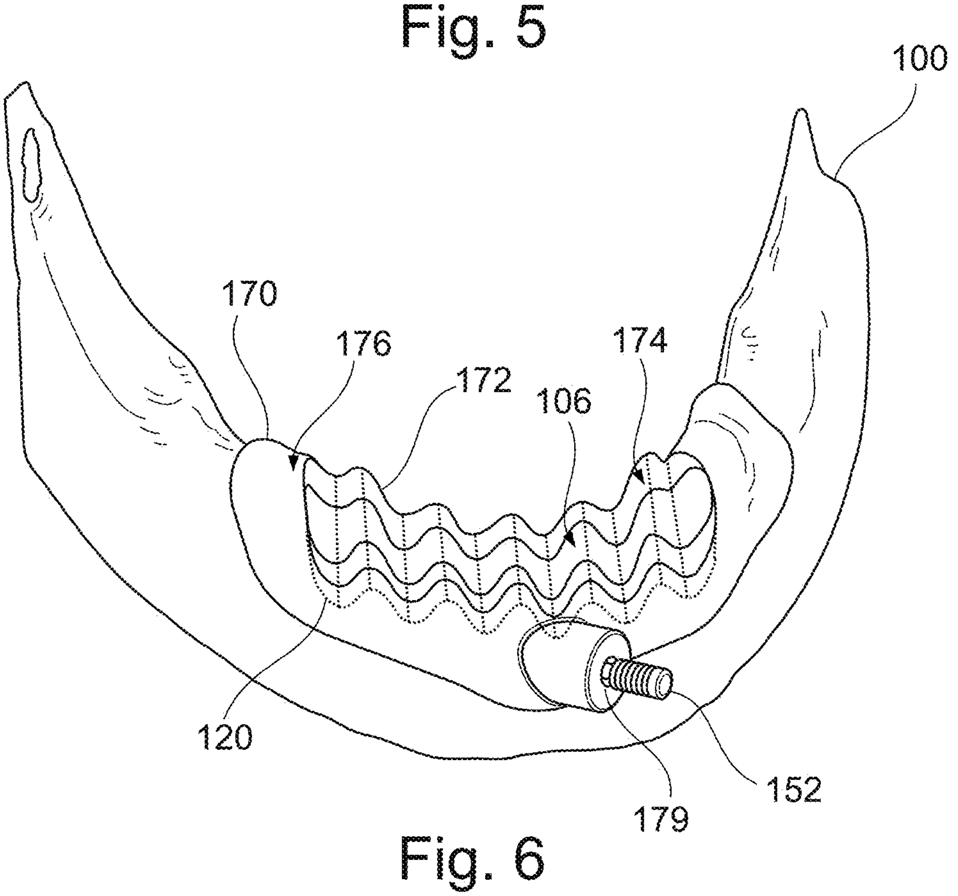
FIG. 6 shows an exemplary three-dimensional digital guide model arranged on an exemplary three-dimensional digital jaw model.

FIG. 6 shows an exemplary three-dimensional digital guide model 170 arranged on the exemplary three-dimensional digital jaw model 100 of FIG. 5 with a section of the three-dimensional digital jaw model 100 cut off by the three-dimensional digital corrugated surface 120 as a cutting surface. The three-dimensional digital guide model 170 is a model of a physical preparation guide. The three-dimensional digital guide model 170 has a form of a splint, which is configured to be arranged on the three-dimensional digital jaw model 100. An inner surface of the splint is defined as a negative of an outer surface of the three-dimensional digital jaw model 100, on which the three-dimensional digital guide model 170 is to be arranged.

The splint formed by the three-dimensional digital guide model 170 comprises a cutout 174 in an occlusal section 176 of the splint. A contour line 172 of the cutout 174 of the three-dimensional digital guide model 170 defines a target contour line of a dental preparation to be applied to the jawbone, in order to prepare it for receiving the implant-supported bridge. The contour line 172 of the cutout 174 is defined by an intersection line, which is defined by the intersection of the three-dimensional digital jaw model 100 overlaid with the three-dimensional digital corrugated surface 120 as shown, e.g., in FIG. 5. The three-dimensional digital corrugated surface 120 is indicated in FIG. 6 by dotted lines.

The three-dimensional digital guide model 170 is, e.g., a model of a bone reduction guide. The bone reduction guide defines by the contour line 172 the target contour line of the preparation. The target contour line is a contour line of an occlusal surface of the jawbone of the patient to be achieved by the dental preparation comprising a bone reduction. A preparation of the jawbone using the contour line 172 of the bone reduction guide as a guidance defining the target contour line of the preparation may result in a preparation surface 106 of the jawbone as shown in FIG. 6.

For generating the three-dimensional digital guide model 170 of the physical preparation guide, the three-dimensional digital jaw model 100 and the three-dimensional digital corrugated surface 120 with the adjusted waveform may be used. For example, a splint with a reception 179 for receiving the fastening means 152 may be arranged on the three-dimensional digital jaw model 100 shown in FIG. 6. The three-dimensional digital jaw model 100 shown in FIG. 6 may result from cutting off a section of the original three-dimensional digital jaw model 100 as shown in FIG. 5. An intersection of the splint of the three-dimensional digital guide model 170 with the three-dimensional digital corrugated surface 120 then result in the cutout 174 with the contour line 172.

Figure 7:
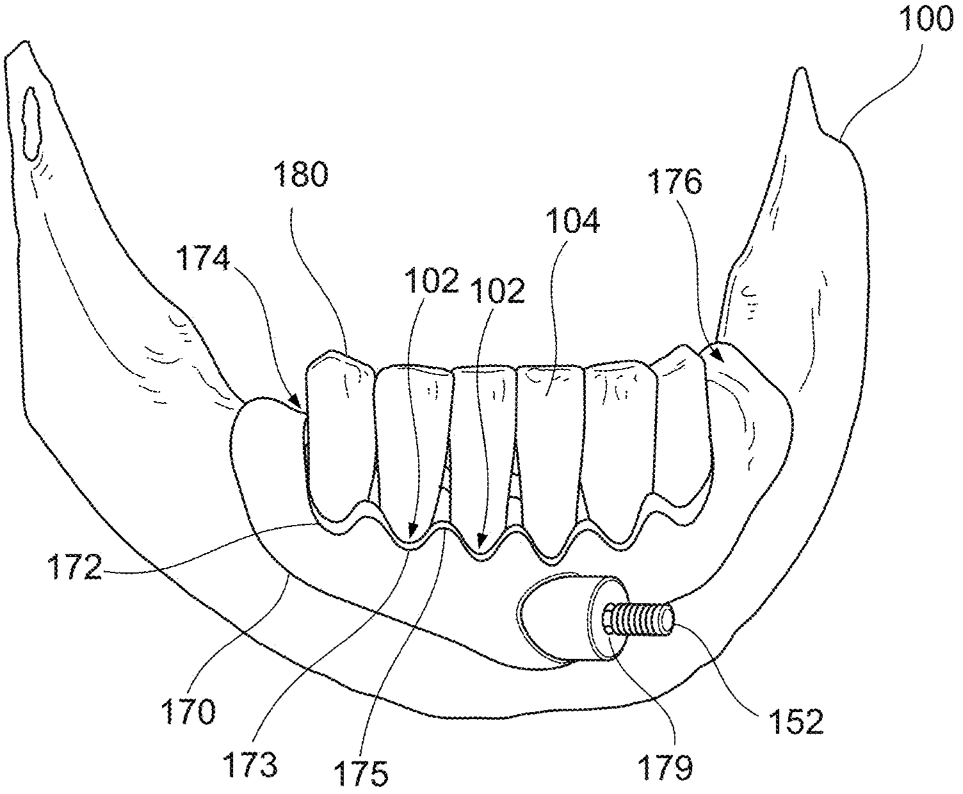
FIG. 7 shows the exemplary three-dimensional digital guide model of FIG. 6 and an implant-supported bridge.

FIG. 7 shows the exemplary three-dimensional digital guide model 170 of FIG. 6 with an implant-supported bridge 180 arranged within the cutout 174 of the three-dimensional digital guide model 170. As shown in FIG. 7 the implant-supported bridge 180 may fit precisely into the cutout 174 with a bottom surface of the implant-supported bridge 180 matching the preparation surface 106 resulting from a preparation of the jawbone defined by the three-dimensional digital jaw model 100 using the three-dimensional digital guide model 170. The implant-supported bridge 180 comprises a plurality of artificial teeth 104. The positions of local minima 173 of the contour line 172, which are defined by the local minima of the waveform of the three-dimensional digital corrugated surface, coincide with the positions of the artificial teeth 104 of the implant-supported bridge 180, when arranged at its predefined position attached to the implants. Local maxima 175 of the contour line 172, which are defined by the local maxima of the waveform of the three-dimensional digital corrugated surface, are arranged between the positions 102 of the artificial teeth 104 of the implant-supported bridge 180.

The implant-supported bridge 180 comprises a plurality of artificial teeth 104. In case of FIG. 7, the implant-supported bridge 180, e.g., comprises six artificial teeth 104.

Figure 8:
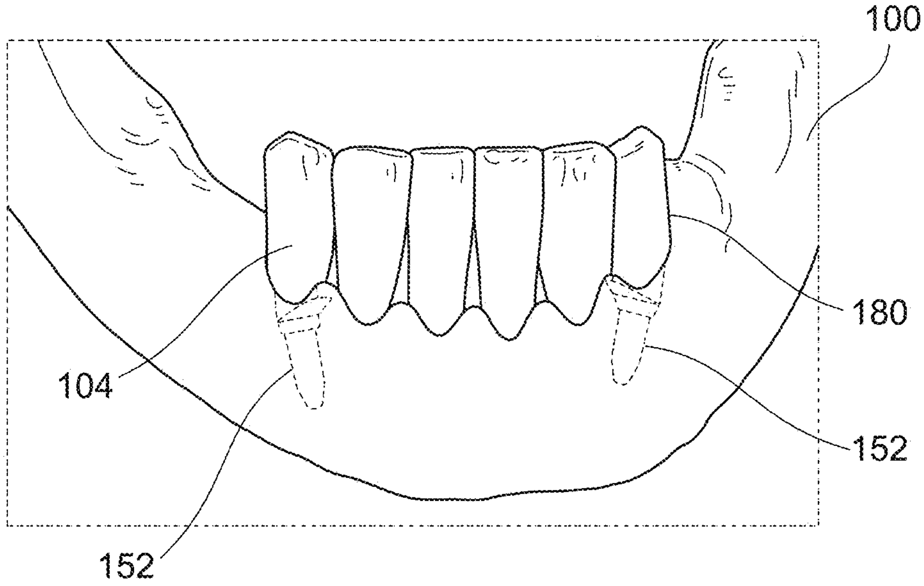
FIG. 8 shows an exemplary three-dimensional digital jaw model of a prepared jaw bone with an implant-supported bridge.

FIG. 8 shows an exemplary three-dimensional digital jaw model 100 of a prepared jaw bone, which has been prepared using the three-dimensional digital guide model 170 shown in FIGS. 6 and 7. On the three-dimensional digital jaw model 100 the implant-supported bridge 180 is arranged. The implant-supported bridge 180 comprises a plurality of artificial teeth 104. In case of FIG. 8, the implant-supported bridge 180, e.g., comprises six artificial teeth 104. The implant-supported bridge 180 is arranged at its predefined position attached to the implants 152. The implants 152 are arranged at their planned positions.

Figure 9:
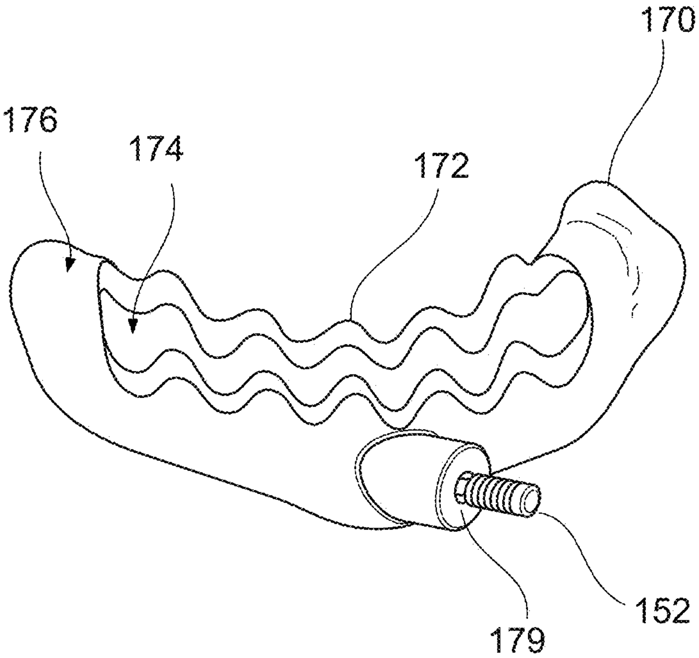
FIG. 9 shows the exemplary three-dimensional digital guide model of FIGS. 6 and 7 configured as a bone reduction guide.

FIG. 9 shows the exemplary the three-dimensional digital guide model 170 of FIGS. 6 and 7. The three-dimensional digital guide model 170 is a model of a physical preparation guide configured as a bone reduction guide. The three-dimensional digital guide model 170 comprises a reception 179 for receiving the fastening means 152. The fastening means 152 is configured for fastening the physical preparation guide defined by the three-dimensional digital guide model 170 to a jawbone.

The three-dimensional digital guide model 170 has a form of a splint. An inner surface of the splint may be defined as a negative of an outer surface of a jaw, on which the splint is to be arranged. The splint comprises a cutout 174 in an occlusal section 176 of the splint. A contour line 172 of the cutout 174 of the three-dimensional digital guide model 170 defines a target contour line of a dental preparation to be applied to the jawbone, in order to prepare it for receiving, e.g., an implant-supported bridge. The target contour line is a contour line of an occlusal surface of the jawbone of the patient to be achieved by the dental preparation comprising a bone reduction.

Figure 10:
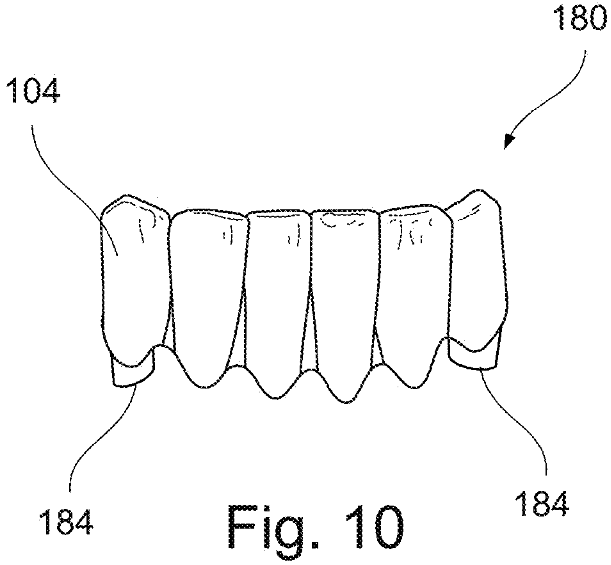
FIG. 10 shows an exemplary implant-supported bridge.

FIG. 10 shows the implant-supported bridge 180 of FIGS. 7 and 8. The implant-supported bridge 180 comprises a plurality of artificial teeth 104. In case of FIG. 10, the implant-supported bridge 180, e.g., comprises six artificial teeth 104. For fastening the implant-supported bridge 180 its predefined position to implants, the implant-supported bridge 180 may comprise abutments 182. The abutments 182 may be used for fastening the implant-supported bridge 180 to the implants using further fastening means, e.g., screws.

Figure 11:
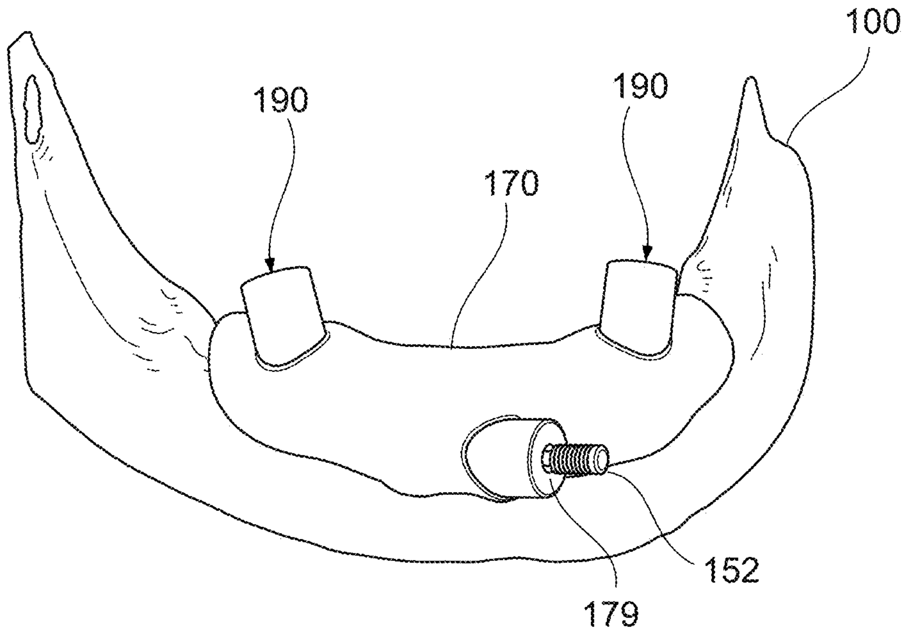
FIG. 11 shows a further exemplary three-dimensional digital guide model arranged on an exemplary three-dimensional digital jaw model.

FIG. 11 shows a further exemplary three-dimensional digital guide model 170 arranged on an exemplary three-dimensional digital jaw model 100. The three-dimensional digital jaw model 100 of a prepared jaw bone, which has been prepared, e.g., using the three-dimensional digital guide model 170 shown in FIGS. 6, 7 and 9. The three-dimensional digital guide model 170 shown in FIGS. 6, 7 and 9 is a model of a physical preparation guide configured as a bone reduction guide, while the physical preparation guide shown in FIG. 11 is a model of a physical preparation guide configured as a drilling guide. The drilling guide comprises through holes 190 defining positions of drilling holes to be drilled into the prepared jawbone as represented by the three-dimensional digital jaw model 100. The drilling holes may be configured for receiving implants 152 to be inserted into the jawbone. The positions of the drilling holes are defined by the planned positions of the implants 152. The three-dimensional digital guide model 170 has the form of a splint being configured to be arranged on the jaw structure defined by the three-dimensional digital jaw model 100. An inner surface of the splint is defined as a negative of an outer surface of the jaw structure. An occlusal section 176 of the splint has an inner surface, which is defined as a negative of a three-dimensional digital corrugated surface with the adjusted waveform. For example, the inner surface is defined as a negative of the three-dimensional digital corrugated surface 120 shown in FIGS. 5 and 6. In addition to the through holes 190, the three-dimensional digital guide model 170 comprises a reception 179 for receiving the fastening means 152. The fastening means 152 is configured for fastening the physical preparation guide defined by the three-dimensional digital guide model 170 to a jawbone.

Figure 12:
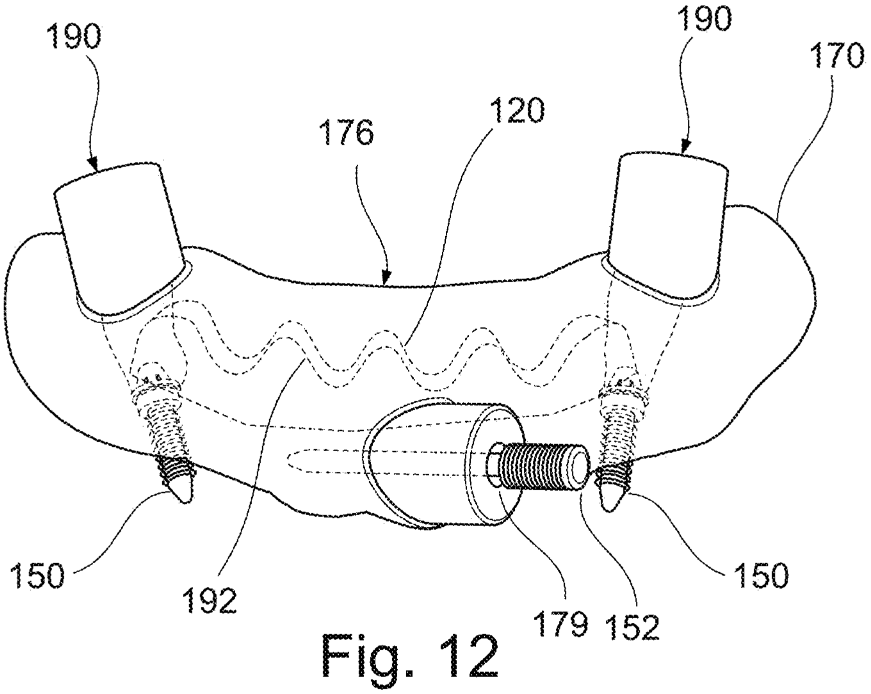
FIG. 12 shows the exemplary three-dimensional digital guide model of FIG. 11 configured as a drilling guide.

FIG. 12 shows the exemplary three-dimensional digital guide model 170 of FIG. 11. In FIG. 11 the implants 152 are shown indicating the planned positions of the implants 152 coinciding with the positions of the through holes 190, such that drilling holes drilled using the drilling guide may be configured for receiving the implants 152 at the planned positions. Furthermore, the fastening means 152, e.g., a screw, received by the reception 179 and extending into the three-dimensional digital guide model 170 is shown. Finally, the inner surface 192 of the occlusal section 176 of the splint formed by the three-dimensional digital guide model 170 is indicated. The inner surface 192 defines as a negative of a three-dimensional digital corrugated surface with the adjusted waveform. For example, the inner surface is defined as a negative of the three-dimensional digital corrugated surface 120 shown in FIGS. 5 and 6.

Figure 13:
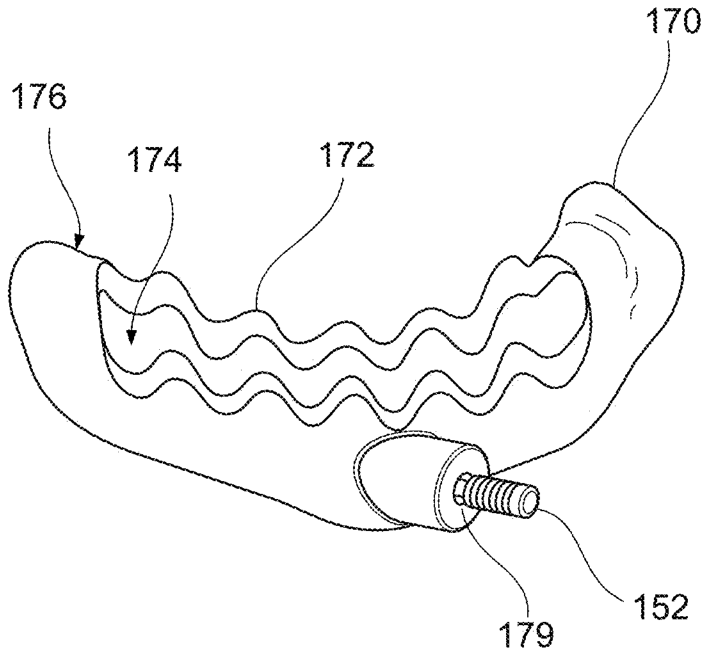
FIG. 13 shows a further exemplary three-dimensional digital guide model configured as a bone reconstruction guide.

FIG. 13 shows an exemplary three-dimensional digital guide model 170 of a physical preparation guide configured as a bone reconstruction guide. The target contour line is a contour line of an occlusal surface of a jawbone of the patient to be achieved by the dental preparation comprising a bone reconstruction.

The three-dimensional digital guide model 170 has a form of a splint, which is configured to be arranged on a three-dimensional digital jaw model. An inner surface of the splint is defined as a negative of an outer surface of the three-dimensional digital jaw model, on which the three-dimensional digital guide model 170 is to be arranged.

The splint formed by the three-dimensional digital guide model 170 comprises a cutout 174 in an occlusal section 176 of the splint. A contour line 172 of the cutout 174 of the three-dimensional digital guide model 170 defines the target contour line of the bone reconstruction.

The contour line 172 of the cutout 174 may be defined by an intersection line, which is defined by the intersection of the splint with a three-dimensional digital corrugated surface as the one, e.g., shown in FIG. 6, when the splint is arranged on a three-dimensional digital jaw model. Thus, the three-dimensional digital jaw model is overlaid with the three-dimensional digital corrugated surface, even though in case of a bone reconstruction there may be no intersection between the three-dimensional digital jaw model and the three-dimensional digital corrugated surface.

A preparation of the jawbone using the contour line 172 of the bone reconstruction guide as a guidance defining the target contour line of the reconstruction may result in a reconstructed occlusal surface of the jawbone with the form of three-dimensional digital corrugated surface.

The three-dimensional digital guide model 170 may comprise a reception 179 for receiving the fastening means 152. The fastening means 152 is configured for fastening the physical preparation guide defined by the three-dimensional digital guide model 170 to a jawbone.

Figure 14:
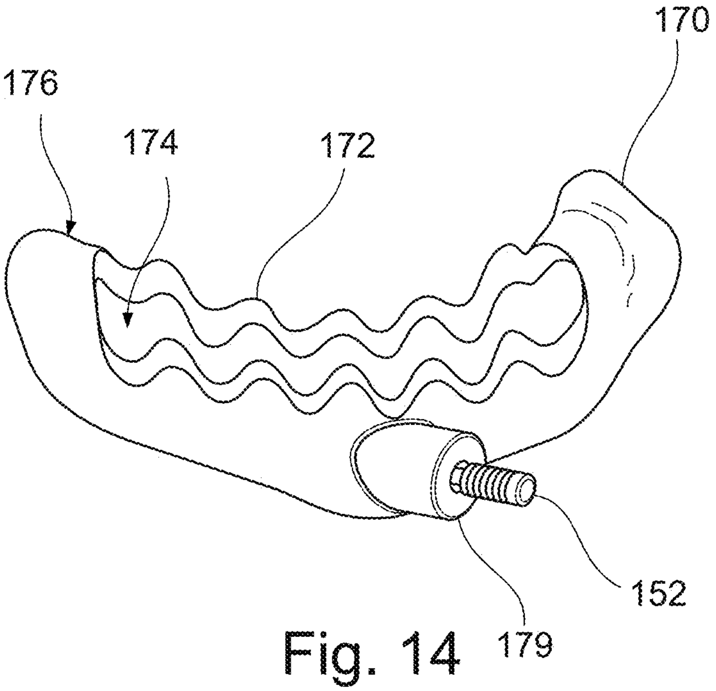
FIG. 14 shows a further exemplary three-dimensional digital guide model configured as a gingiva shaping guide.

FIG. 14 shows an exemplary three-dimensional digital guide model 170 of a physical preparation guide configured as a gingiva shaping guide. The gingiva shaping guide may be configured to prepare a jaw structure in form of a gingiva of a patient to be prepared.

The three-dimensional digital guide model 170 has a form of a splint, which is configured to be arranged on a three-dimensional digital jaw model. The received three-dimensional digital jaw model may define the jaw structure in form of the gingiva. An inner surface of the splint is defined as a negative of an outer surface of the three-dimensional digital jaw model, on which the three-dimensional digital guide model 170 is to be arranged.

The splint formed by the three-dimensional digital guide model 170 comprises a cutout 174 in an occlusal section 176 of the splint. A contour line 172 of the cutout 174 of the three-dimensional digital guide model 170 defines the target contour line for the gingiva shaping. The target contour line is an occlusal contour line of the gingiva of the patient to be achieved by the dental preparation, i.e., the shaping of the gingiva in case of the gingiva shaping guide.

The contour line 172 of the cutout 174 may be defined by an intersection line, which is defined by the intersection of the splint with a three-dimensional digital corrugated surface as the one, e.g., shown in FIG. 6, when the splint is arranged on a three-dimensional digital jaw model. A preparation of the gingiva using the contour line 172 of the gingiva shaping guide as a guidance defining the target contour line for the gingiva shaping may result in a gingiva with, at least sectional, the form of three-dimensional digital corrugated surface.

The three-dimensional digital guide model 170 may comprise a reception 179 for receiving the fastening means 152. The fastening means 152 is configured for fastening the physical preparation guide defined by the three-dimensional digital guide model 170 to a jawbone.

Figure 15:
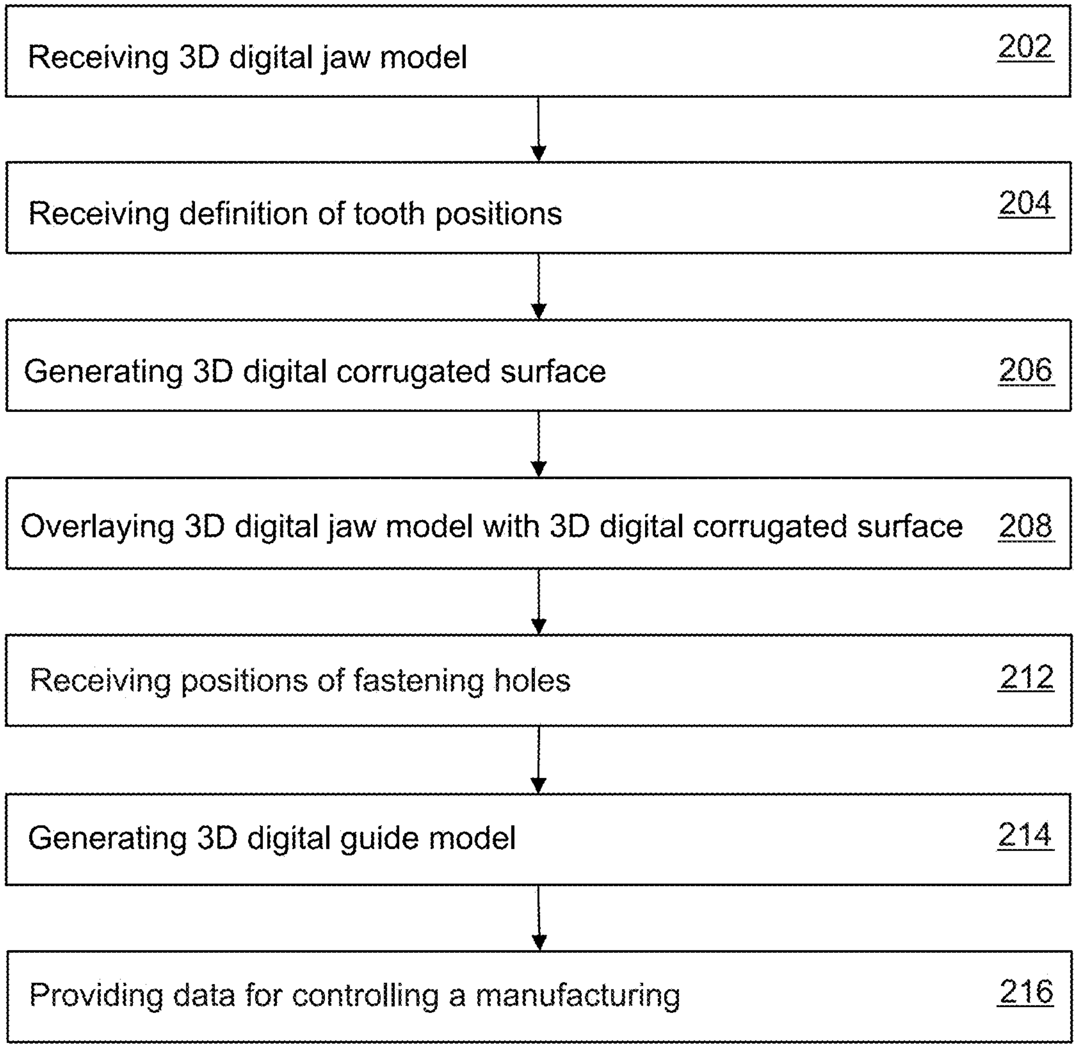
FIG. 15 shows a flowchart illustrating an exemplary method for generating a three-dimensional digital guide model.

FIG. 15 shows an exemplary method for generating a three-dimensional digital guide model of a physical preparation guide for a dental preparation of a patient's jaw. In block 202, a three-dimensional digital jaw model of the patient's jaw is received. In block 204, a definition of tooth positions of a set of teeth comprising a plurality of teeth is received. The tooth positions comprise one or more target tooth positions for one or more artificial teeth comprised by the set of teeth. For example, all teeth comprised by the set of teeth are artificial teeth and all tooth positions received are target positions of the artificial teeth of the set of teeth. For example, the set of teeth comprises one or more artificial teeth as well one or more natural teeth. For example, the set of teeth comprises a full dental arch. For example, the full dental arch is a full dental arch of artificial teeth. For example, the full dental arch comprises one or more artificial teeth as well as one or more natural teeth. For example, the set of teeth comprises a partial dental arch. For example, the partial dental arch is a partial dental arch of artificial teeth. For example, the partial dental comprises one or more artificial teeth as well as one or more natural teeth.

In block 206, a three-dimensional digital corrugated surface is generated. The corrugation of the three-dimensional digital corrugated surface is defined by a waveform comprising local minima and maxima. The three-dimensional digital corrugated surface extends along a reference plane extending perpendicular to a longitudinal direction of the teeth, while the corrugation extends in the longitudinal direction.

The minima, e.g., are formed by first straight lines of a first constant height extending in oral direction parallel to the reference plane through the target positions of the teeth. The maxima, e.g., are formed by second straight lines of a second constant height extending in oral direction parallel to the reference plane between the target positions of the teeth.

In block 208, the three-dimensional digital jaw model is overlaid with the three-dimensional digital corrugated surface. The overlaying comprises adjusting the waveform using the tooth positions, such that the local minima of the waveform are arranged at the positions of the teeth, while the local maxima of the waveform are arranged between the positions of the teeth. For example, the overlaying comprising a graphically overlaying the three-dimensional digital jaw model with the three-dimensional digital corrugated surface.

In block 212, definitions of positions of fastening holes are received. The fastening holes are configured for receiving fastening means for fastening the physical guide model to the patient's jaw. The definitions of the fastening holes ae defining positions of one or more through holes to be comprised by the three-dimensional digital guide model. The second holes are configured for receiving fastening means for fastening the physical guide model to the patient's jaw.

In block 214, the three-dimensional digital guide model of the physical preparation guide is generated using the three-dimensional digital corrugated surface with the adjusted waveform and the three-dimensional digital jaw model. For example, the three-dimensional digital guide model has a form of a splint being configured to be arranged on a jaw structure defined by the received three-dimensional digital jaw model with an inner surface of the splint being defined as a negative of an outer surface of the jaw structure. The generating of the three-dimensional digital guide model further comprises defining the through holes using the definitions of the positions of the fastening holes received in block 214.

For example, the physical preparation guide defines a target contour line of the dental preparation. The splint comprises a cutout in an occlusal section of the splint with a contour line of the cutout being defined by an intersection line, which is defined by the intersection of the three-dimensional digital jaw model overlaid with the three-dimensional digital corrugated surface with the adjusted waveform.

For example, the jaw structure defined by the received three-dimensional digital jaw model comprises a representation of a jawbone of the patient to be prepared. For example, the three-dimensional digital jaw model comprises scan data of the jawbone of the patient, e.g., CBCT scan data and/or CT scan data.

For example, the jaw structure defined by the received three-dimensional digital jaw model comprises a representation of intraoral issue of the patient comprising the gingiva of the patient. For example, the three-dimensional digital jaw model, e.g., comprises optical scan data of the intraoral issue of the patient comprising the gingiva of the patient. The optical scan data may, e.g., comprise intraoral optical scan data or optical scan data from a scan of a classical mold/impression of the intraoral issue of the patient.

For example, the physical preparation guide is a bone reduction guide and the target contour line is a contour line of an occlusal surface of a jawbone of the patient to be achieved by the dental preparation comprising a bone reduction. The bone reduction, e.g., comprises removing bone material from the jawbone.

For example, the physical preparation guide is a bone reconstruction guide and the target contour line is a contour line of an occlusal surface of a jawbone of the patient to be achieved by the dental preparation comprising a bone reconstruction. The bone reconstruction, e.g., comprises adding reconstruction material to the jawbone.

For example, the jaw structure defined by the received three-dimensional digital jaw model is a gingiva of the patient to be prepared. The physical preparation guide, e.g., is a gingiva shaping guide and the target contour line is an occlusal contour line of the gingiva of the patient to be achieved by the dental preparation comprising a shaping of the gingiva of the patient. The shaping of the gingiva, e.g., comprises removing gingiva material from the gingiva. For example, the three-dimensional digital jaw model comprises optical scan data of the gingiva of the patient.

In block 216, data for controlling a manufacturing of the physical preparation guide is provided. The data defines the three-dimensional digital guide model as a template for the physical preparation guide.

Figure 16:
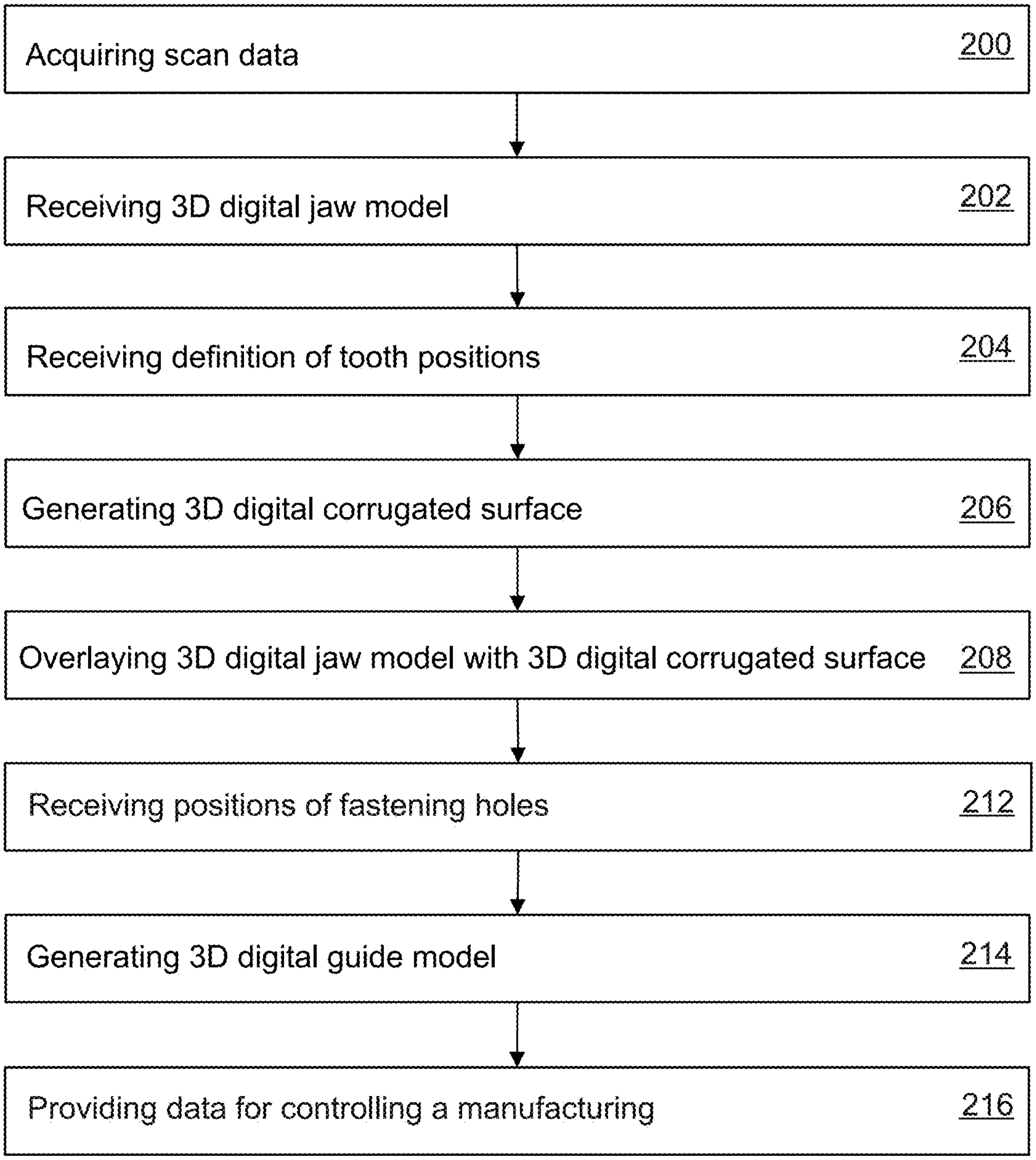
FIG. 16 shows a flowchart illustrating a further exemplary method for generating a three-dimensional digital guide model.

FIG. 16 shows a further exemplary method for generating a three-dimensional digital guide model of a physical preparation guide for a dental preparation of a patient's jaw. The method of FIG. 16 comprises an acquisition of the scan data in block 200. The acquired scan data, e.g., comprises CBCT scan data acquired using an CBCT scanning system. The acquired scan data, e.g., comprises CT scan data acquired using an CT scanning system. The acquired scan data, e.g., comprises optical scan data acquired using an optical scanning system.

Blocks 202 to 216 of FIG. 15 are identical to blocks 202 to 216 of FIG. 15. The scan data acquired in block 200 provides the three-dimensional digital jaw model of the patient's jaw, which is received in block 202.

Figure 17:
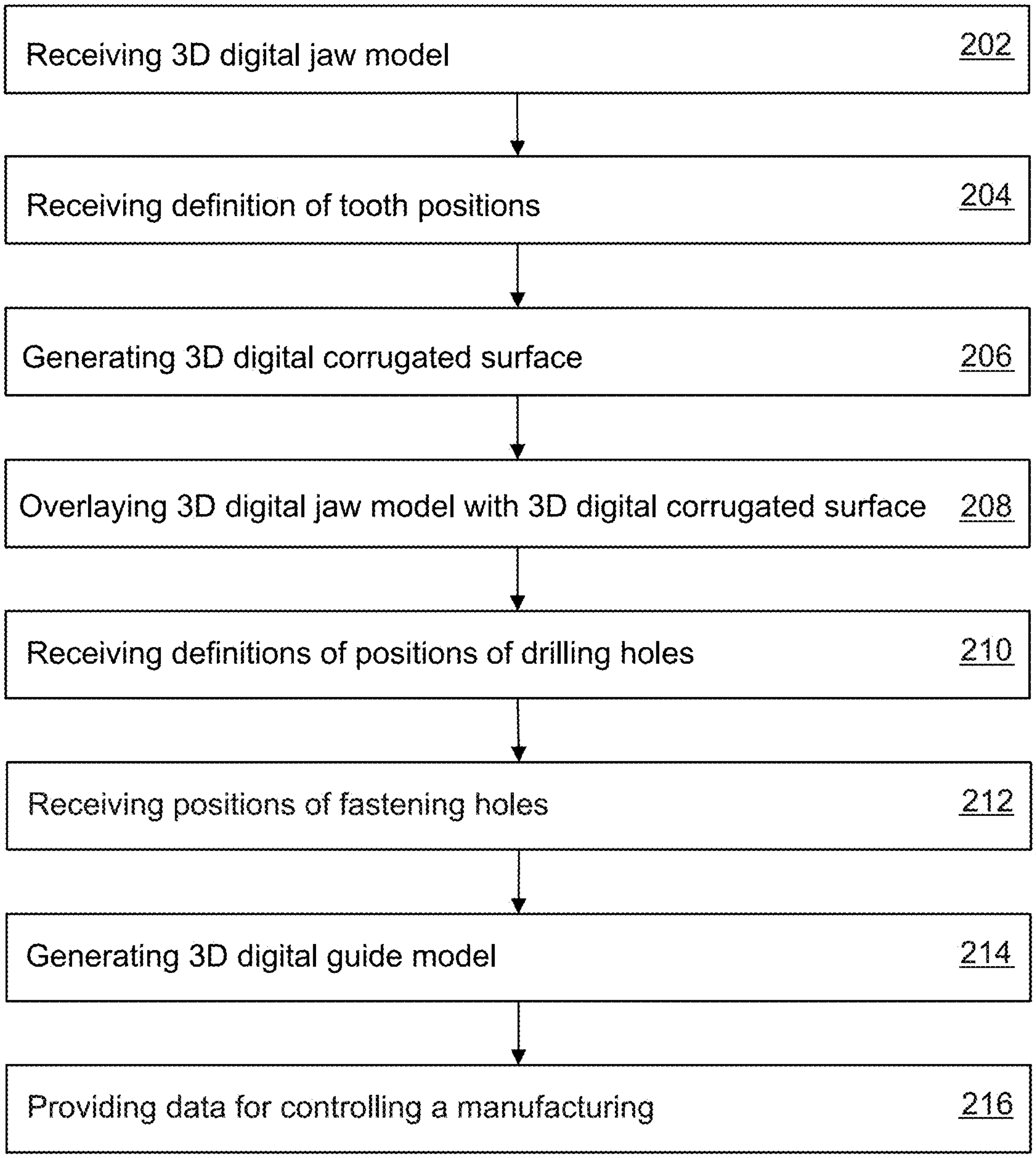
FIG. 17 shows a flowchart illustrating a further exemplary method for generating a three-dimensional digital guide model.

FIG. 17 shows an exemplary method for generating a three-dimensional digital guide model of a physical preparation guide for a dental preparation of a patient's jaw. For example, the physical preparation guide being generated is a drilling guide. The In block 202, a three-dimensional digital jaw model of the patient's jaw is received. For example, the jaw structure defined by the received three-dimensional digital jaw model represents a jawbone of the patient to be prepared. For example, the three-dimensional digital jaw model comprises scan data of the jawbone of the patient, e.g., CBCT scan data and/or CT scan data.

For example, the jaw structure defined by the received three-dimensional digital jaw model comprises a representation of intraoral issue of the patient comprising the gingiva of the patient. For example, the three-dimensional digital jaw model, e.g., comprises optical scan data of the intraoral issue of the patient comprising the gingiva of the patient. The optical scan data may, e.g., comprise intraoral optical scan data or optical scan data from a scan of a classical mold/impression of the intraoral issue of the patient.

In block 204, a definition of tooth positions of a set of teeth comprising a plurality of teeth is received. The tooth positions comprise one or more target tooth positions for one or more artificial teeth comprised by the set of teeth. For example, all teeth comprised by the set of teeth are artificial teeth and all tooth positions received are target positions of the artificial teeth of the set of teeth. For example, the set of teeth comprises one or more artificial teeth as well one or more natural teeth. For example, the set of teeth comprises a full dental arch. For example, the full dental arch is a full dental arch of artificial teeth. For example, the full dental arch comprises one or more artificial teeth as well as one or more natural teeth. For example, the set of teeth comprises a partial dental arch. For example, the partial dental arch is a partial dental arch of artificial teeth. For example, the partial dental comprises one or more artificial teeth as well as one or more natural teeth.

In block 206, a three-dimensional digital corrugated surface is generated. The corrugation of the three-dimensional digital corrugated surface is defined by a waveform comprising local minima and maxima. The three-dimensional digital corrugated surface extends along a reference plane extending perpendicular to a longitudinal direction of the teeth, while the corrugation extends in the longitudinal direction.

The minima, e.g., are formed by first straight lines of a first constant height extending in oral direction parallel to the reference plane through the target positions of the teeth. The maxima, e.g., are formed by second straight lines of a second constant height extending in oral direction parallel to the reference plane between the target positions of the teeth.

In block 208, the three-dimensional digital jaw model is overlaid with the three-dimensional digital corrugated surface. The overlaying comprises adjusting the waveform using the tooth positions, such that the local minima of the waveform are arranged at the positions of the teeth, while the local maxima of the waveform are arranged between the positions of the teeth. For example, the overlaying comprising a graphically overlaying the three-dimensional digital jaw model with the three-dimensional digital corrugated surface.

In block 210, definitions of the positions of drilling holes to be drilled into the jawbone of the patient for implants are received.

In block 212, definitions of positions of fastening holes are received. The fastening holes are configured for receiving fastening means for fastening the physical guide model to the patient's jaw. The definitions of the fastening holes ae defining positions of one or more second through holes to be comprised by the three-dimensional digital guide model. The second through holes are configured for receiving fastening means for fastening the physical guide model to the patient's jaw.

In block 214, the three-dimensional digital guide model of the physical preparation guide is generated using the three-dimensional digital corrugated surface with the adjusted waveform and the three-dimensional digital jaw model. The three-dimensional digital guide model has a form of a splint being configured to be arranged on a jaw structure defined by the received three-dimensional digital jaw model with an inner surface of the splint being defined as a negative of an outer surface of the jaw structure. For example, the physical preparation guide being generated is a drilling guide, which comprises first through holes defining positions of drilling holes to be drilled into the jawbone of the patient for implants. The occlusal section of the splint, e.g., has an inner surface defined as a negative of the three-dimensional digital corrugated surface with the adjusted waveform. The generating of the three-dimensional digital guide model comprises defining the first through holes using the definitions of the positions of the drilling holes received in block 212. The generating of the three-dimensional digital guide model further comprises defining the second through holes using the definitions of the positions of the fastening holes received in block 214.

In block 216, data for controlling a manufacturing of the physical preparation guide is provided. The data defines the three-dimensional digital guide model as a template for the physical preparation guide.

Figure 18:
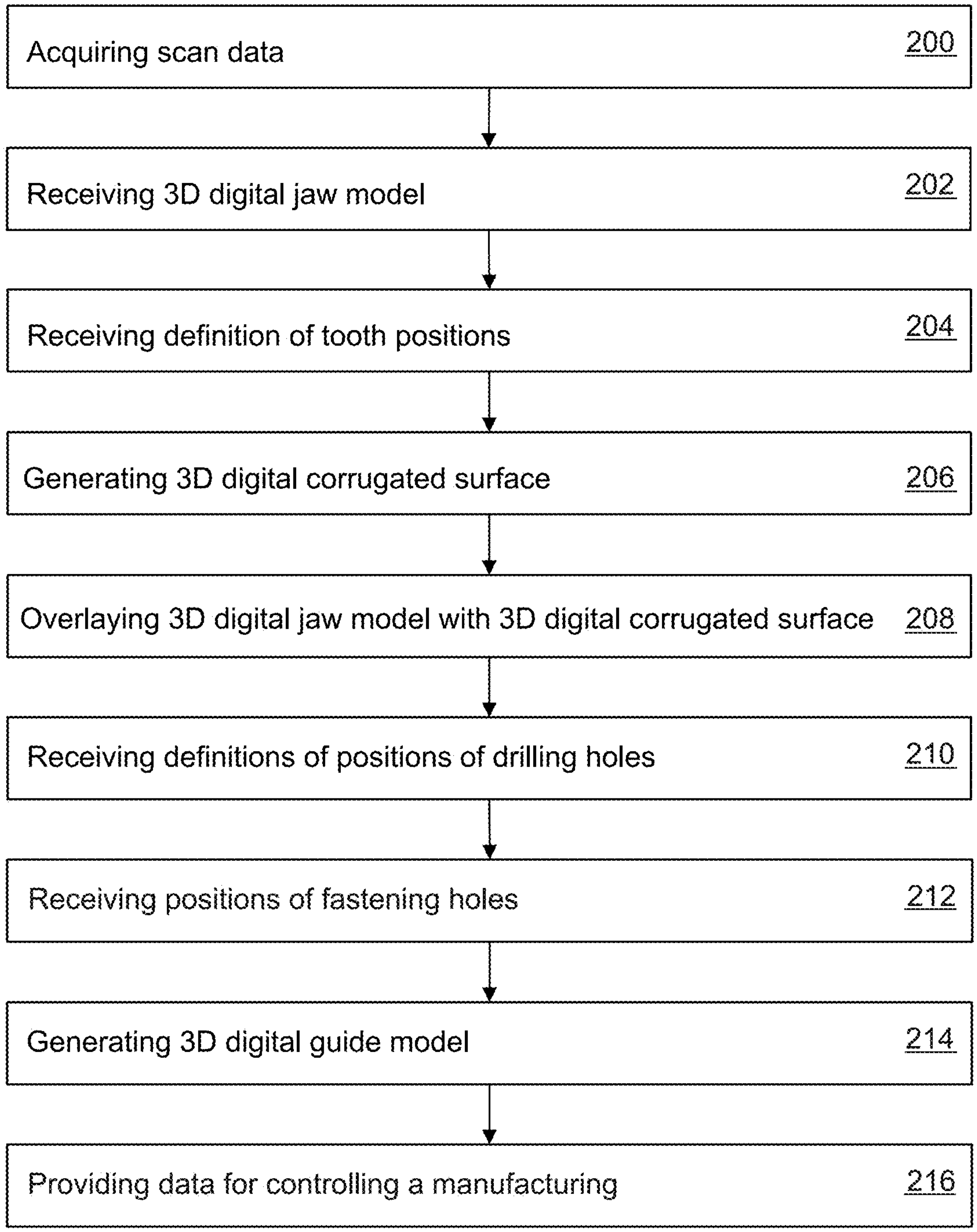
FIG. 18 shows a flowchart illustrating a further exemplary method for generating a three-dimensional digital guide model.

FIG. 18 shows a further exemplary method for generating a three-dimensional digital guide model of a physical preparation guide for a dental preparation of a patient's jaw. The method of FIG. 18 comprises an acquisition of the scan data in block 200. The acquired scan data, e.g., comprises CBCT scan data acquired using an CBCT scanning system. The acquired scan data, e.g., comprises CT scan data acquired using an CT scanning system. The acquired scan data, e.g., comprises optical scan data acquired using an optical scanning system.

Blocks 202 to 216 of FIG. 18 are identical to blocks 202 to 216 of FIG. 16. The scan data acquired in block 200 provides the three-dimensional digital jaw model of the patient's jaw, which is received in block 202.

Figure 19:
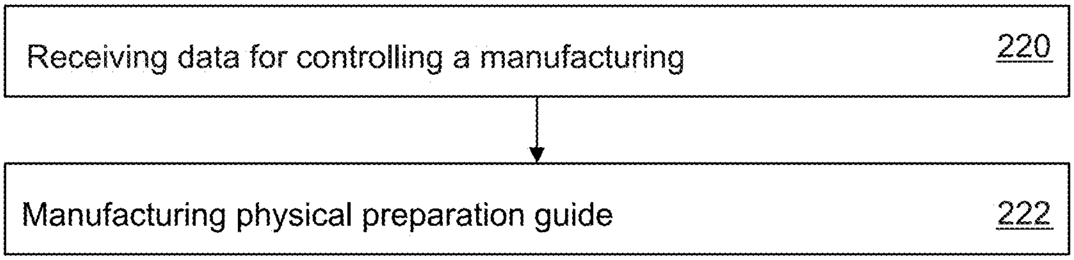
FIG. 19 shows a flowchart illustrating a further exemplary method for manufacturing a preparation guide.

FIG. 19 shows a further exemplary method for manufacturing a physical preparation guide. In block 220, data for controlling a manufacturing of the physical preparation guide is received. The data defines a three-dimensional digital guide model as a template for the physical preparation guide. The data received in block 220 is, e.g., the data for controlling the manufacturing of the physical preparation guide provided in block 216 of FIG. 15 to FIG. 18.

In block 222, the physical preparation guide is manufactured using the data for controlling the manufacturing received in block 220. The manufactured physical preparation guide is a physical copy of the template defined by the provided data. For example, the manufactured physical preparation guide is one of the following: a bone reduction guide, a bone reconstruction guide, a gingiva shaping guide, or a drilling guide.

Figure 20:
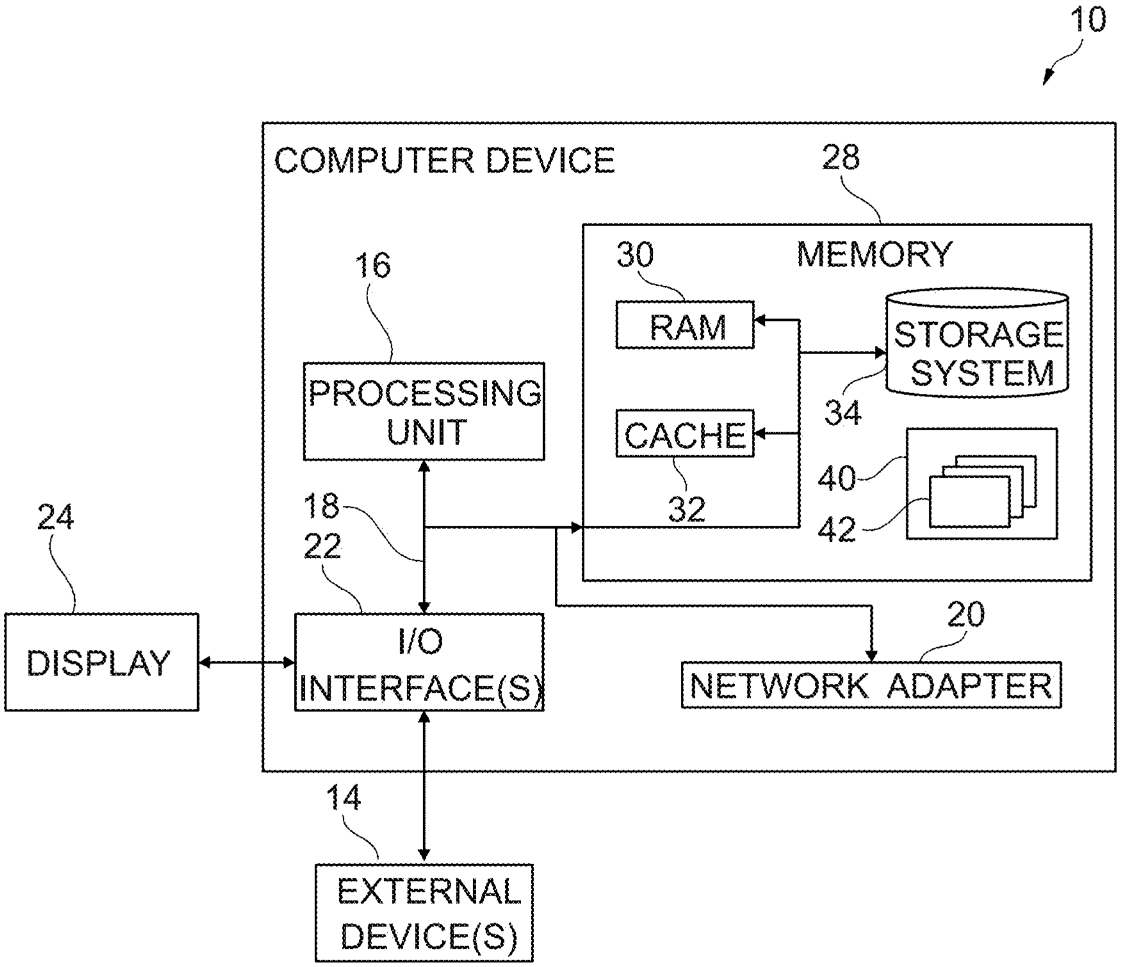
FIG. 20 shows an exemplary computer device for generating a three-dimensional digital guide model.

FIG. 20 shows a schematic diagram of an exemplary computer device 10 for generating a three-dimensional digital guide model of a physical preparation guide for a dental preparation of a patient's jaw. The computer device 10 may be operational with numerous other general-purpose or special-purpose computing system environments or configurations. Computer device 10 may be described in the general context of computer device executable instructions, such as program modules comprising executable program instructions, being executable by the computer device 10. Generally, program modules may include routines, programs, objects, components, logic, data structures, and so on that perform particular tasks or implement particular abstract data types. Computer device 10 may be practiced in distributed computing environments where tasks are performed by remote processing devices that are linked through a communications network. In a distributed computing environment, program modules may be located in both local and remote computer device storage media including memory storage devices.

In FIG. 20, computer device 10 is shown in the form of an exemplary general-purpose computing device. The components of computer device 10 may include, but are not limited to, one or more processors or processing units 16, a system memory 28, and a bus 18 that couples various system components including system memory 28 to processor 16. Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer device 10 may comprise a variety of computer device readable storage media. Such media may be any available storage media accessible by computer device 10, and include both volatile and non-volatile storage media, removable and non-removable storage media.

A system memory 28 may include computer device readable storage media in the form of volatile memory, such as random-access memory (RAM) 30 and/or cache memory 32. Computer device 10 may further include other removable/non-removable, volatile/non-volatile computer device storage media. For example, storage system 34 may be provided for reading from and writing to a non-removable, non-volatile magnetic media also referred to as a hard drive. For example, a magnetic disk drive for reading from and writing to a removable, non-volatile magnetic disk, e.g., a floppy disk, and an optical disk drive for reading from or writing to a removable, non-volatile optical disk such as a CD-ROM, DVD-ROM or other optical storage media may be provided. In such instances, each storage medium may be connected to bus 18 by one or more data media interfaces. Memory 28 may, e.g., include a three-dimensional digital jaw model of the patient's jaw. The three-dimensional digital guide model may define a jaw structure, on which a preparation guide is to be arranged. The jaw structure may, e.g., be a jawbone and/or a gingiva to be prepared. The three-dimensional digital jaw model may, e.g., represent a jawbone and/or a gingiva of the patient to be prepared. The three-dimensional digital jaw model may comprise scan data the patient's jaw. For example, the scan data may comprise CBCT scan data or CT scan data.

Memory 28 may, e.g., include scan data of a patient's mouth. The scan data may, e.g., comprise CBCT scan data or CT scan data of the patient's mouth. The scan data may provide information about the patent's jawbone. The scan data may, e.g., comprise optical scan data of the patient's mouth. The optical scan data may, e.g., comprise intraoral optical scan data or optical scan data from a scan of a classical mold/impression, e.g., providing information about the surface structure of the patient's intraoral tissue comprising teeth and the gingiva.

Memory 28 may, e.g., include a definition of tooth positions of a set of teeth comprising a plurality of teeth, the tooth positions comprising one or more target tooth positions for one or more artificial teeth comprised by the set of teeth.

Memory 28 may, e.g., include a three-dimensional digital corrugated surface. The three-dimensional digital corrugated surface may be generated using the computer device 10. The corrugation of the three-dimensional digital corrugated surface may be defined by a waveform comprising local minima and maxima. The three-dimensional digital corrugated surface may extend along a reference plane extending perpendicular to a longitudinal direction of the teeth, with the corrugation extending in the longitudinal direction.

The three-dimensional digital corrugated surface included by the memory 28 may be adjusted using the tooth positions. The adjusting may be executed using the computer device 10. The waveform defining the three-dimensional digital corrugated surface may be adjusted using the tooth positions, such that the local minima of the waveform are arranged at the positions of the teeth, while the local maxima of the waveform are arranged between the positions of the teeth. Alternatively, the memory 28 may, e.g., include in addition to a non-adjusted three-dimensional digital corrugated surface an adjusted three-dimensional digital corrugated surface. The non-adjusted three-dimensional digital corrugated surface an adjusted three-dimensional digital corrugated surface may be generated using the computer device 10.

Memory 28 may, e.g., include one or more three-dimensional digital guide models of one or more physical preparation guides. The three-dimensional digital guide models may be generated using the three-dimensional digital corrugated surface with the adjusted waveform and the three-dimensional digital jaw model. For the generating of the one or more three-dimensional digital guide models, the computer device 10 may be used.

Memory 28 may, e.g., include data for controlling a manufacturing of the physical preparation guide. The data defining the three-dimensional digital guide model as a template for the physical preparation guide. The data for controlling a manufacturing of the physical preparation guide may be provided using the computer device 10.

Memory 28 may, e.g., include a three-dimensional digital restoration model of a dental restoration to be arranged at the patient's prepared jaw. To prepare the patient's jaw, the one or more preparation guides defined by the one or more three-dimensional digital guide model may be generated. The dental restoration may, e.g., an implant supported artificial tooth. For example, the dental restoration may be an implant supported crown. The dental restoration may, e.g., an implant supported set of artificial teeth. For example, the dental restoration may be an implant supported crown. The three-dimensional digital restoration model may, e.g., be generated using the computer device 10. Memory 28 may, e.g., include a digital tooth library providing a plurality of three-dimensional digital library tooth models. This digital tooth library may be used for providing the three-dimensional models of the artificial tooth of the three-dimensional digital restoration model.

Program 40 may have a set of one or more program modules 42 and by way of example be stored in memory 28. The program modules 42 may comprise an operating system, one or more application programs, other program modules, and/or program data. Each of these program modules 42, i.e., the operating system, the one or more application programs, the other program modules, and/or the program data or some combination thereof, may include an implementation of a networking environment. One or more of the program modules 42 may be configured for executing a method for generating the three-dimensional digital guide model of the physical preparation guide for the dental preparation of the patient's jaw. One or more of the program modules 42 may be configured for controlling a manufacturing of the physical preparation guide. One or more of the program modules 42 may, e.g., be configured for executing one or more of the methods of FIGS. 15 to 19.

Computer device 10 may further communicate with one or more external devices 14 such as a keyboard, a pointing device, like a mouse, and a display 24 enabling a user to interact with computer device 10. Such communication can occur via input/output (I/O) interfaces 22. Computer device 10 may further communicate with one or more networks such as a local area network (LAN), a general wide area network (WAN), and/or a public network, like the Internet, via network adapter 20. Network adapter 20 may communicate with other components of computer device 10 via bus 18. It should be understood that although not shown, other hardware and/or software components could be used in conjunction with computer device 10.

Figure 21:
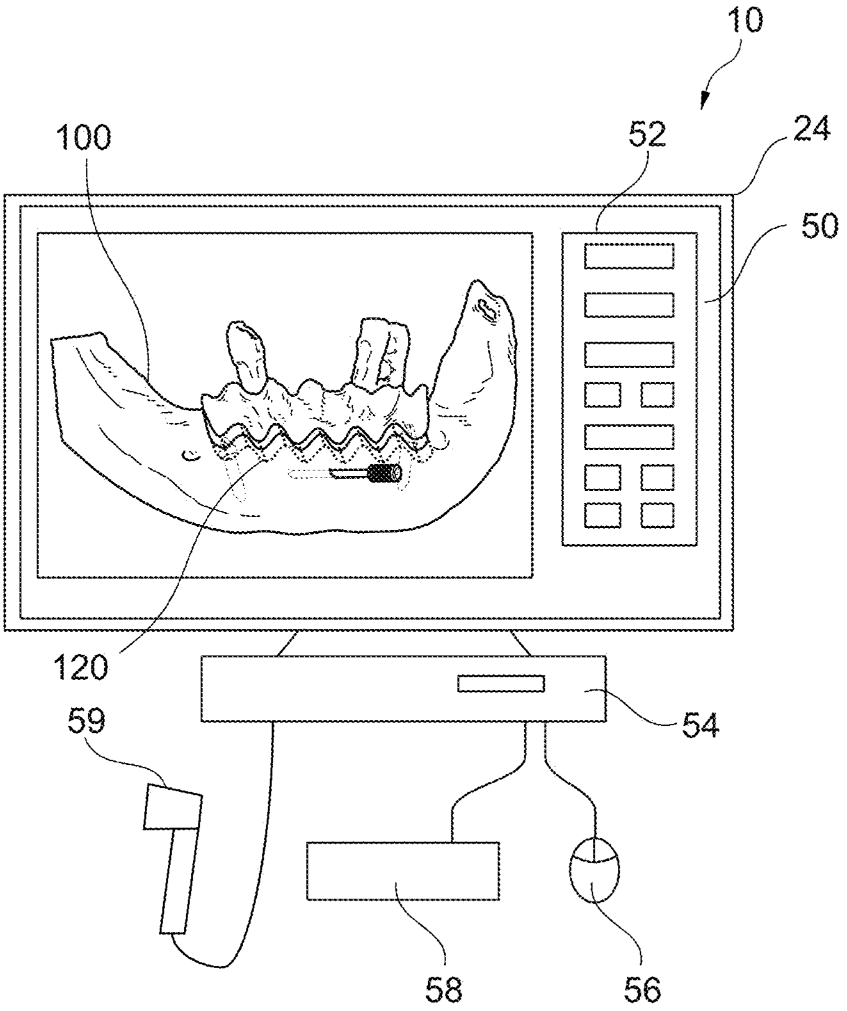
FIG. 21 shows an exemplary computer device for generating a three-dimensional digital guide model.

The computer device 10 shown in FIG. 21 may be configured for generating a three-dimensional digital guide model of a physical preparation guide for a dental preparation of a patient's jaw. The method comprises receiving a three-dimensional digital jaw model of the patient's jaw. A definition of tooth positions of a set of teeth comprising a plurality of teeth is received. The tooth positions comprise one or more target tooth positions for one or more artificial teeth comprised by the set of teeth. A three-dimensional digital corrugated surface is generated. The corrugation of the three-dimensional digital corrugated surface is defined by a waveform comprising local minima and maxima. The three-dimensional digital corrugated surface extends along a reference plane extending perpendicular to a longitudinal direction of the teeth, while the corrugation extends in the longitudinal direction.

The three-dimensional digital jaw model is overlaid with the three-dimensional digital corrugated surface. The overlaying comprises adjusting the waveform using the tooth positions, such that the local minima of the waveform are arranged at the positions of the teeth, while the local maxima of the waveform are arranged between the positions of the teeth. The three-dimensional digital guide model of the physical preparation guide is generated using the three-dimensional digital corrugated surface with the adjusted waveform and the three-dimensional digital jaw model. Data for controlling a manufacturing of the physical preparation guide is provided. The data defines the three-dimensional digital guide model as a template for the physical preparation guide.

The computer device 10 shown in FIG. 21 may, e.g., further be configured for controlling a manufacturing of the physical preparation guide. The data provided for controlling the manufacturing may be used for this purpose with the manufactured physical preparation guide being a physical copy of the template defined by the provided data.

FIG. 21 shows an exemplary computer device 10 for generating a three-dimensional digital guide model of a physical preparation guide for a dental preparation of a patient's jaw. The computer device 10 may, e.g., be configured as shown in FIG. 20. The computer device 10 may comprise a hardware component 54 comprising one or more processors as well as a memory storing machine-executable program instructions. Execution of the program instructions by the one or more processors may cause the one or more processors to control the computer device 10 to, e.g., generate the three-dimensional digital guide model of the physical preparation guide for the dental preparation of the patient's jaw and to provide data for controlling a manufacturing of the physical preparation guide.

The computer device 10 may further comprise one or more input devices, like a keyboard 58 and a mouse 56, enabling a user to interact with the computer device 10. Furthermore, the computer device 10 may comprise one or more output devices, like a display 24 providing a graphical user interface 50 with control elements 52, e.g., GUI elements, enabling the user to control the generating of the three-dimensional digital guide model of the physical preparation guide for the dental preparation of the patient's jaw. The computer device 10 may further comprise an exemplary scanner 59 configured for scanning a patient's mouth. The scanner 59 may, e.g., comprise an CT or CBCT scanning system. The scanner 59 may, e.g., comprise an optical scanner configured for scanning, e.g., a patient's oral cavity, an imprint of a patient's oral cavity and/or a positive of a patient's oral cavity generated using an imprint.

Figure 22:
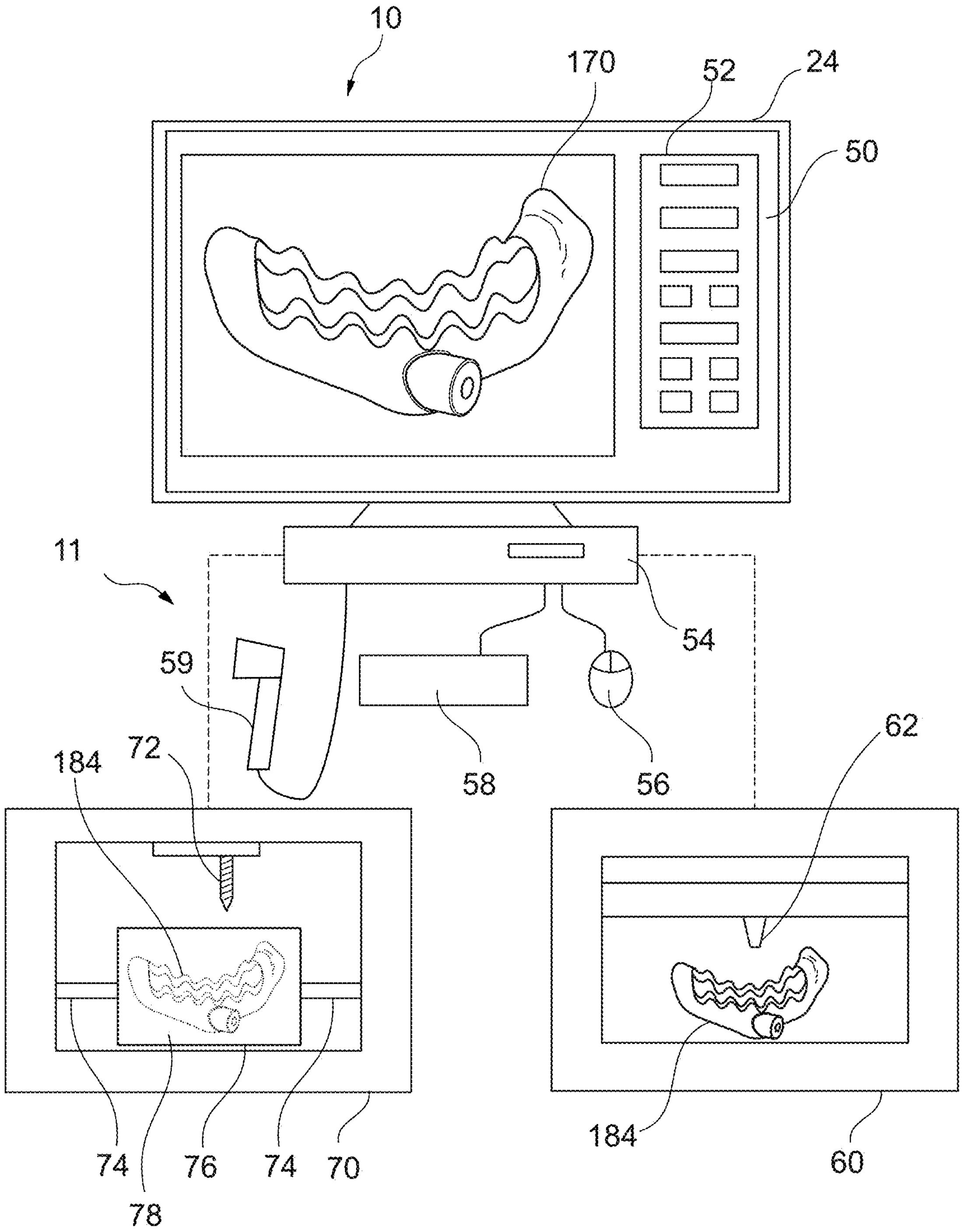
FIG. 22 shows an exemplary system for manufacturing a physical preparation guide.

FIG. 22 shows an exemplary manufacturing system 11 for manufacturing one or more physical preparation guides 184. For manufacturing the one or more physical preparation guides 184, data may be used provided for controlling the manufacturing. The data provided for controlling the manufacturing of the one or more physical preparation guides 184 may define one or more three-dimensional digital guide models 170 as templates for the physical preparation guides 184. The one or more manufactured physical preparation guides 184 may be physical copies of the templates defined by the provided data.

The manufacturing system 11 may comprise the computer device 10 of FIG. 21. The computer device 10 may further be configured to control one or more manufacturing devices 60, 70. For controlling the one or more manufacturing devices 60, 70 a processing unit of the computer device 10 may execute program instructions. Execution of the program instructions by the processing unit may cause the computer device 10 to control the one or more manufacturing devices 60, 70 to manufacture the one or more physical guide models 184 using the data provided for controlling the manufacturing.

For example, the manufacturing system 11 may comprise a manufacturing device in form of a machining device 70 controlled by the computer device 10. The machining device 70 may be configured to machining a blank 76 using one or more machining tools 72. The blank 76 of raw material 78, may be provided using one or more holding devices 74 and cut into a desired shape and size of the element to be manufactured, e.g., a physical guide models 184. The machining tool 72 may, e.g., be a milling tool.

For example, the manufacturing system 11 may comprise a manufacturing device in form of a three-dimensional (3D) printing device 60. The 3D printing device 60 may be controlled by the computer device 10 and configured to print an element to be manufactured, e.g., a physical guide models 184. The 3D printing device 60 may comprise a printing element 62 configured to generate the respective element, like the physical guide model 184, layer by layer. The printing element 62 may, e.g., comprise a nozzle configured for distributing printing material.

In case the element to be manufactured using the 3D printing device 60 is made using metal, the 3D printing device 60 may, e.g., be configured for executing selective laser sintering, laser melting or electron beam melting. Selective laser sintering uses a laser for sintering a powdered material, aiming the laser automatically at points in space defined by a three-dimensional digital model of the element to be printed. The laser energy may result in a local sintering of the powdered material, binding the material together to create a solid structure. For example, the printing element 62 of the 3D printing device 60 may comprise a laser and/or a distributing device for distributing the powdered material. In case of laser melting, the laser is used for locally melting the powdered material, binding the material together to create a solid structure. Selective electron beam melting uses an electron beam for melting a powdered material, aiming the electron beam automatically at points in space defined by a three-dimensional digital model of the element to be printed. The beam energy may result in a local melting of the powdered material, binding the material together to create a solid structure. For example, the printing element 62 of the 3D printing device 60 may comprise an electron beam emitter and/or a distributing device for distributing the powdered material.

For example, the three-dimensional digital restoration model may be used as a positive to define a negative of the physical guide model 184 in form of a negative three-dimensional digital guide model. The negative three-dimensional digital guide model may be used to manufacture, e.g., using machining device 70 or 3D printing device 60, a casting matrix. The casting matrix may be configured for casting the physical guide model 184 by inserting casting material into the casting matrix and curing the inserted casting material.

The physical guide model 184 may, e.g., be a bone reduction guide as depicted in FIG. 22. The physical guide model 184 may alternatively, e.g., be a bone reconstruction guide, a drilling guide or a gingiva shaping guide.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage. Any reference signs in the claims should not be construed as limiting the scope.

A single processor or other unit may fulfill the functions of several items recited in the claims. A computer program may be stored/distributed on a suitable medium, such as an optical storage medium or a solid-state medium supplied together with or as part of other hardware, but may also be distributed in other forms, such as via the Internet or other wired or wireless telecommunication systems.

As will be appreciated by one skilled in the art, aspects of the present invention may be embodied as an apparatus, method, computer program or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon. A computer program comprises the computer executable code or "program instructions".

Any combination of one or more computer readable medium(s) may be utilized. The computer readable medium may be a computer readable signal medium or a computer readable storage medium. A "computer-readable storage medium" as used herein encompasses any tangible storage medium which may store instructions which are executable by a processor of a computing device, also referred to as a processing unit. The computer-readable storage medium may be referred to as a computer-readable non-transitory storage medium. The computer-readable storage medium may also be referred to as a tangible computer readable medium. For example, a computer-readable storage medium may also be able to store data which is able to be accessed by the processor of the computing device. Examples of computer-readable storage media include, but are not limited to: a floppy disk, a magnetic hard disk drive, a solid-state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. A further example of an optical disk may be a Blu-ray disk. The term computer readable-storage medium also refers to various types of recording media capable of being accessed by the computer device via a network or communication link. For example, a data may be retrieved over a modem, over the internet, or over a local area network. Computer executable code embodied on a computer readable medium may be transmitted using any appropriate medium, including but not limited to wireless, wireline, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

"Computer memory" or "memory" is an example of a computer-readable storage medium. Computer memory is any memory which is directly accessible to a processor. "Computer storage" or "storage" is a further example of a computer-readable storage medium. Computer storage is any non-volatile computer-readable storage medium. For example, computer storage may also be computer memory or vice versa.

A "processor" or "processing unit" as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer device or distributed amongst multiple computer devices. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object-oriented programming language such as Java, Smalltalk, C++ or the like and conventional procedural programming languages, such as the "C" programming language or similar programming languages and compiled into machine executable instructions. In some instances, the computer executable code may be in the form of a high-level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Generally, the program instructions can be executed on one processor or on several processors. In the case of multiple processors, they can be distributed over several different entities like clients, servers etc. Each processor could execute a portion of the instructions intended for that entity. Thus, when referring to a system or process involving multiple entities, the computer program or program instructions are understood to be adapted to be executed by a processor associated or related to the respective entity.

A "user interface" as used herein is an interface which allows a user or operator to interact with a computer or computer device. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer to indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, gear sticks, steering wheel, pedals, wired glove, dance pad, remote control, one or more switches, one or more buttons, and accelerometer are all examples of user interface components which enable the receiving of information or data from an operator.

A GUI element is a data object some of which's attributes specify the shape, layout and/or behavior of an area displayed on a graphical user interface, e.g., a screen. A GUI element can be a standard GUI element such as a button, a text box, a tab, an icon, a text field, a pane, a check-box item or item group or the like. A GUI element can likewise be an image, an alphanumeric character or any combination thereof. At least some of the properties of the displayed GUI elements depend on the data value aggregated on the group of data object said GUI element represents.

Aspects of the present invention are described with reference to flowchart illustrations and/or block diagrams of methods, apparatus (systems) and computer program products. It will be understood that each block or a portion of the blocks of the flowchart, illustrations, and/or block diagrams, can be implemented by computer program instructions in form of computer executable code when applicable. It is further understood that, when not mutually exclusive, combinations of blocks in different flowcharts, illustrations, and/or block diagrams may be combined. These computer program instructions may be provided to a processor of a general-purpose computer, special-purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer-implemented process such that the instructions which execute on the computer or other programmable apparatus provide processes for implementing the functions/acts specified in the flowchart and/or block diagram block or blocks.

Although the invention may have been described in reference to specific examples, it should be understood that the invention is not limited to these examples only and that many variations of these examples may be readily envisioned by the skilled person after having read the present disclosure. The invention may thus further be described without limitation by the following examples.

1. A method for generating a three-dimensional digital guide model of a physical preparation guide for a dental preparation of a patient's jaw,
   the method comprising:
   receiving a three-dimensional digital jaw model of the patient's jaw,
   receiving a definition of tooth positions of a set of teeth comprising a plurality of teeth, the tooth positions comprising one or more target tooth positions for one or more artificial teeth comprised by the set of teeth,
   generating a three-dimensional digital corrugated surface, the corrugation of the three-dimensional digital corrugated surface being defined by a waveform comprising local minima and maxima, the three-dimensional digital corrugated surface extending along a reference plane extending perpendicular to a longitudinal direction of the teeth, with the corrugation extending in the longitudinal direction,
   overlaying the three-dimensional digital jaw model with the three-dimensional digital corrugated surface, the overlaying comprising adjusting the waveform using the tooth positions, such that the local minima of the waveform are arranged at the positions of the teeth, while the local maxima of the waveform are arranged between the positions of the teeth,
   generating the three-dimensional digital guide model of the physical preparation guide using the three-dimensional digital corrugated surface with the adjusted waveform and the three-dimensional digital jaw model,
   providing data for controlling a manufacturing of the physical preparation guide, the data defining the three-dimensional digital guide model as a template for the physical preparation guide.
2. The method of feature combination 1, the minima being formed by first straight lines of a first constant height extending in oral direction parallel to the reference plane through the target positions of the teeth, the maxima being formed by second straight lines of a second constant height extending in oral direction parallel to the reference plane between the target positions of the teeth.
3. The method of any of the previous feature combinations, the three-dimensional digital guide model having a form of a splint being configured to be arranged on a jaw structure defined by the received three-dimensional digital jaw model with an inner surface of the splint being defined as a negative of an outer surface of the jaw structure.
4. The method of feature combination 3, the physical preparation guide defining a target contour line of the dental preparation,
   the splint comprising a cutout in an occlusal section of the splint with a contour line of the cutout being defined by an intersection line, which is defined by the intersection of the three-dimensional digital jaw model overlaid with the three-dimensional digital corrugated surface with the adjusted waveform.
5. The method of feature combination 4, the jaw structure defined by the received three-dimensional digital jaw model representing a jawbone of the patient to be prepared.
6. The method of feature combination 5, the physical preparation guide being a bone reduction guide with the target contour line being a contour line of an occlusal surface of a jawbone of the patient to be achieved by the dental preparation comprising a bone reduction.
7. The method of feature combination 5, the physical preparation guide being a bone reconstruction guide with the target contour line being a contour line of an occlusal surface of a jawbone of the patient to be achieved by the dental preparation comprising a bone reconstruction.
8. The method of any of the previous feature combinations 3 to 7, the three-dimensional digital jaw model comprising scan data the patient's jaw.
9. The methos of feature combination 8, the scan data comprising one or more of the following: CBCT scan data, CT scan data.
10. The method of feature combination 4, the jaw structure defined by the received three-dimensional digital jaw model being a gingiva of the patient to be prepared,
    the physical preparation guide being a gingiva shaping guide with the target contour line being an occlusal contour line of the gingiva of the patient to be achieved by the dental preparation comprising a shaping of the gingiva of the patient.
11. The method of feature combination 3, the physical preparation guide being a drilling guide comprising first through holes defining positions of drilling holes to be drilled into the jawbone of the patient for implants,
    the occlusal section of the splint having an inner surface being defined as a negative of the three-dimensional digital corrugated surface with the adjusted waveform,
    the method further comprising:
    receiving definitions of the positions of the drilling holes,
    the generating of the three-dimensional digital guide model comprising defining the first through holes using the definitions of the positions of the drilling holes.
12. The method of any of the previous feature combinations, the method further comprising:
    defining positions of one or more second through holes to be comprised by the three-dimensional digital guide model, the second through holes being configured for receiving fastening means for fastening the physical guide model to the patient's jaw, the definitions of the positions of the second through holes being used for the generating of the three-dimensional digital guide model comprising the one or more second through holes.

13. The method of any of the previous feature combinations, all teeth comprised by the set of teeth being artificial teeth, all tooth positions received being target positions of the artificial teeth of the set of teeth.

14. The method of feature combination 13, the set of teeth comprising a full dental arch of artificial teeth.

15. The method of any of the previous feature combinations, the method further comprising manufacturing of the physical preparation guide using the data provided for controlling the manufacturing with the manufactured physical preparation guide being a physical copy of the template defined by the provided data.

16. A computer program for generating a three-dimensional digital guide model of a physical preparation guide for a dental preparation of a patient's jaw, the computer program comprising program instructions executable by a processor of a computer device to cause the computer device to:

receive a three-dimensional digital jaw model of the patient's jaw, receive a definition of tooth positions of a set of teeth comprising a plurality of teeth, the tooth positions comprising one or more target tooth positions for one or more artificial teeth comprised by the set of teeth, generate a three-dimensional digital corrugated surface, the corrugation of the three-dimensional digital corrugated surface being defined by a waveform comprising local minima and maxima, the three-dimensional digital corrugated surface extending along a reference plane extending perpendicular to a longitudinal direction of the teeth, with the corrugation extending in the longitudinal direction, overlay the three-dimensional digital jaw model with the three-dimensional digital corrugated surface, the overlaying comprising adjusting the waveform using the tooth positions, such that the local minima of the waveform are arranged at the positions of the teeth, while the local maxima of the waveform are arranged between the positions of the teeth, generate the three-dimensional digital guide model of the physical preparation guide using the three-dimensional digital corrugated surface with the adjusted waveform and the three-dimensional digital jaw model, provide data for controlling a manufacturing of the physical preparation guide, the data defining the three-dimensional digital guide model as a template for the physical preparation guide.

17. A computer program product for generating a three-dimensional digital guide model of a physical preparation guide for a dental preparation of a patient's jaw, the computer program product comprising a non-transitory computer readable storage medium having program instructions embodied therewith, the program instructions being executable by a processor of a computer device to cause the computer device to:

receive a three-dimensional digital jaw model of the patient's jaw, receive a definition of tooth positions of a set of teeth comprising a plurality of teeth, the tooth positions comprising one or more target tooth positions for one or more artificial teeth comprised by the set of teeth, generate a three-dimensional digital corrugated surface, the corrugation of the three-dimensional digital corrugated surface being defined by a waveform comprising local minima and maxima, the three-dimensional digital corrugated surface extending along a reference plane extending perpendicular to a longitudinal direction of the teeth, with the corrugation extending in the longitudinal direction, overlay the three-dimensional digital jaw model with the three-dimensional digital corrugated surface, the overlaying comprising adjusting the waveform using the tooth positions, such that the local minima of the waveform are arranged at the positions of the teeth, while the local maxima of the waveform are arranged between the positions of the teeth, generate the three-dimensional digital guide model of the physical preparation guide using the three-dimensional digital corrugated surface with the adjusted waveform and the three-dimensional digital jaw model, provide data for controlling a manufacturing of the physical preparation guide, the data defining the three-dimensional digital guide model as a template for the physical preparation guide.

18. A computer device for generating a three-dimensional digital guide model of a physical preparation guide for a dental preparation of a patient's jaw, the computer device comprising a processor and a memory storing program instructions executable by the processor, execution of the program instructions by the processor causing the computer device to:

receive a three-dimensional digital jaw model of the patient's jaw, receive a definition of tooth positions of a set of teeth comprising a plurality of teeth, the tooth positions comprising one or more target tooth positions for one or more artificial teeth comprised by the set of teeth, generate a three-dimensional digital corrugated surface, the corrugation of the three-dimensional digital corrugated surface being defined by a waveform comprising local minima and maxima, the three-dimensional digital corrugated surface extending along a reference plane extending perpendicular to a longitudinal direction of the teeth, with the corrugation extending in the longitudinal direction, overlay the three-dimensional digital jaw model with the three-dimensional digital corrugated surface, the overlaying comprising adjusting the waveform using the tooth positions, such that the local minima of the waveform are arranged at the positions of the teeth, while the local maxima of the waveform are arranged between the positions of the teeth, generate the three-dimensional digital guide model of the physical preparation guide using the three-dimensional digital corrugated surface with the adjusted waveform and the three-dimensional digital jaw model, provide data for controlling a manufacturing of the physical preparation guide, the data defining the three-dimensional digital guide model as a template for the physical preparation guide.

19. A manufacturing system comprising the computer device of feature combination 18, the manufacturing system further comprising one or more manufacturing devices configured to manufacture the physical guide model, execution of the program instructions by the processor further causing the computer device to control the one or more manufacturing devices to manufacture the physical guide model using the data provided for controlling the manufacturing with the manufactured physical preparation guide being a physical copy of the template defined by the data provided.

REFERENCE SIGNS LIST

| | |
|---|---|
| 10 | computer device |
| 11 | manufacturing system |
| 14 | external device |
| 16 | processing unit |
| 18 | bus |
| 20 | network adapter |
| 22 | I/O interface |
| 24 | display |
| 28 | memory |
| 30 | RAM |
| 32 | cache |
| 34 | storage system |
| 40 | program |
| 42 | program module |
| 50 | user interface |
| 52 | control elements |
| 54 | hardware device |
| 56 | keyboard |
| 58 | mouse |
| 59 | scanner |
| 60 | 3D printing device |
| 62 | printing element |
| 70 | machining device |
| 72 | machining tool |
| 74 | holding device |
| 76 | blank |
| 78 | raw material |
| 100 | 3D digital jaw model |
| 102 | position of tooth |
| 104 | 3D digital tooth model |
| 106 | preparation surface |
| 120 | digital corrugated surfaces |
| 122 | local minimum |
| 124 | local maximum |
| 126 | reference plane |
| 128 | longitudinal direction |
| 130 | first straight line |
| 132 | second straight line |
| 134 | oral direction |
| 136 | tooth arch |
| 150 | implant |
| 152 | fastening means |
| 170 | 3D digital guide model |
| 172 | contour line |
| 173 | local minimum |
| 174 | cutout |
| 175 | local maximum |
| 176 | occlusal section |
| 180 | implant-supported bridge |
| 182 | abutment |
| 184 | physical guide model |
| 190 | through hole |
| 192 | inner surface |
| $h_1$ | first constant height |
| $h_2$ | second constant height |
| $\Delta h$ | height difference |

The invention claimed is:

1. A method for generating a three-dimensional digital guide model of a physical preparation guide for a dental preparation of a patient's jaw, the method comprising:

receiving a three-dimensional digital jaw model of the patient's jaw, receiving a definition of tooth positions of a set of teeth comprising a plurality of teeth, the tooth positions comprising one or more target tooth positions for one or more artificial teeth comprised by the set of teeth, generating a three-dimensional digital corrugated surface, the corrugation of the three-dimensional digital corrugated surface being defined by a waveform comprising local minima and maxima, the three-dimensional digital corrugated surface extending along a reference plane extending perpendicular to a longitudinal direction of the teeth, with the corrugation extending in the longitudinal direction, overlaying the three-dimensional digital jaw model with the three-dimensional digital corrugated surface, the overlaying comprising adjusting the waveform using the tooth positions, such that the local minima of the waveform are arranged at the positions of the teeth, while the local maxima of the waveform are arranged between the positions of the teeth, generating the three-dimensional digital guide model of the physical preparation guide using the three-dimensional digital corrugated surface with the adjusted waveform and the three-dimensional digital jaw model, providing data for controlling a manufacturing of the physical preparation guide, the data defining the three-dimensional digital guide model as a template for the physical preparation guide, manufacturing the physical preparation guide using the data provided for controlling the manufacturing, the manufactured physical preparation guide being a physical copy of the template defined by the provided data.

2. The method of claim 1, the minima being formed by first straight lines of a first constant height extending in oral direction parallel to the reference plane through the target positions of the teeth, the maxima being formed by second straight lines of a second constant height extending in oral direction parallel to the reference plane between the target positions of the teeth.

3. The method of claim 1, the three-dimensional digital guide model having a form of a splint being configured to be arranged on a jaw structure defined by the received three-dimensional digital jaw model with an inner surface of the splint being defined as a negative of an outer surface of the jaw structure.

4. The method of claim 3, the physical preparation guide defining a target contour line of the dental preparation, the splint comprising a cutout in an occlusal section of the splint with a contour line of the cutout being defined by an intersection line, which is defined by the intersection of the three-dimensional digital jaw model overlaid with the three-dimensional digital corrugated surface with the adjusted waveform.

5. The method of claim 4, the jaw structure defined by the received three-dimensional digital jaw model representing a jawbone of the patient to be prepared.

6. The method of claim 5, the physical preparation guide being a bone reduction guide with the target contour line being a contour line of an occlusal surface of a jawbone of the patient to be achieved by the dental preparation comprising a bone reduction.

7. The method of claim 5, the physical preparation guide being a bone reconstruction guide with the target contour line being a contour line of an occlusal surface of a jawbone of the patient to be achieved by the dental preparation comprising a bone reconstruction.

8. The method of claim 3, the three-dimensional digital jaw model comprising scan data of the patient's jaw.

9. The method of claim 8, the scan data comprising one or more of the following: CBCT scan data, CT scan data.

10. The method of claim 4, the jaw structure defined by the received three-dimensional digital jaw model being a gingiva of the patient to be prepared, the physical preparation guide being a gingiva shaping guide with the target contour line being an occlusal contour line of the gingiva of the patient to be achieved by the dental preparation comprising a shaping of the gingiva of the patient.

11. The method of claim 3, the physical preparation guide being a drilling guide comprising first through holes defining positions of drilling holes to be drilled into the jawbone of the patient for implants, the occlusal section of the splint having an inner surface being defined as a negative of the three-dimensional digital corrugated surface with the adjusted waveform, the method further comprising:

receiving definitions of the positions of the drilling holes, the generating of the three-dimensional digital guide model comprising defining the first through holes using the definitions of the positions of the drilling holes.

12. The method of claim 1, the method further comprising:

defining positions of one or more second through holes to be comprised by the three-dimensional digital guide model, the second through holes being configured for receiving fastening means for fastening the physical guide model to the patient's jaw, the definitions of the positions of the second through holes being used for the generating of the three-dimensional digital guide model comprising the one or more second through holes.

13. The method of claim 1, all teeth comprised by the set of teeth being artificial teeth, all tooth positions received being target positions of the artificial teeth of the set of teeth.

14. The method of claim 13, the set of teeth comprising a full dental arch of artificial teeth.

15. The method of claim 1, the manufacturing of the physical preparation guide comprising one or more of the following: a computer-controlled additive method, a computer-controlled subtractive method.

16. A computer program product for generating a three-dimensional digital guide model of a physical preparation guide for a dental preparation of a patient's jaw, the computer program product comprising a non-transitory computer readable storage medium having program instructions embodied therewith, the program instructions being executable by a processor of a computer device to cause the computer device to:

receive a three-dimensional digital jaw model of the patient's jaw, receive a definition of tooth positions of a set of teeth comprising a plurality of teeth, the tooth positions comprising one or more target tooth positions for one or more artificial teeth comprised by the set of teeth, generate a three-dimensional digital corrugated surface, the corrugation of the three-dimensional digital corrugated surface being defined by a waveform comprising local minima and maxima, the three-dimensional digital corrugated surface extending along a reference plane extending perpendicular to a longitudinal direction of the teeth, with the corrugation extending in the longitudinal direction, overlay the three-dimensional digital jaw model with the three-dimensional digital corrugated surface, the overlaying comprising adjusting the waveform using the tooth positions, such that the local minima of the waveform are arranged at the positions of the teeth, while the local maxima of the waveform are arranged between the positions of the teeth, generate the three-dimensional digital guide model of the physical preparation guide using the three-dimensional digital corrugated surface with the adjusted waveform and the three-dimensional digital jaw model, provide data for controlling a manufacturing of the physical preparation guide, the data defining the three-dimensional digital guide model as a template for the physical preparation guide, control one or more manufacturing devices to manufacture the physical preparation guide using the data provided for controlling the manufacturing, the manufactured physical preparation guide being a physical copy of the template defined by the provided data.

17. A manufacturing system comprising a computer device for generating a three-dimensional digital guide model of a physical preparation guide for a dental preparation of a patient's jaw, the computer device comprising a processor and a memory storing program instructions executable by the processor, execution of the program instructions by the processor causing the computer device to:

receive a three-dimensional digital jaw model of the patient's jaw, receive a definition of tooth positions of a set of teeth comprising a plurality of teeth, the tooth positions comprising one or more target tooth positions for one or more artificial teeth comprised by the set of teeth, generate a three-dimensional digital corrugated surface, the corrugation of the three-dimensional digital corrugated surface being defined by a waveform comprising local minima and maxima, the three-dimensional digital corrugated surface extending along a reference plane extending perpendicular to a longitudinal direction of the teeth, with the corrugation extending in the longitudinal direction, overlay the three-dimensional digital jaw model with the three-dimensional digital corrugated surface, the overlaying comprising adjusting the waveform using the tooth positions, such that the local minima of the waveform are arranged at the positions of the teeth, while the local maxima of the waveform are arranged between the positions of the teeth, generate the three-dimensional digital guide model of the physical preparation guide using the three-dimensional digital corrugated surface with the adjusted waveform and the three-dimensional digital jaw model, provide data for controlling a manufacturing of the physical preparation guide, the data defining the three-dimensional digital guide model as a template for the physical preparation guide, the manufacturing system further comprising one or more manufacturing devices configured to manufacture the physical guide model, execution of the program instructions by the processor further causing the computer device to control the one or more manufacturing devices to manufacture the physical guide model using the data provided for controlling the manufacturing with the manufactured physical preparation guide being a physical copy of the template defined by the data provided.

* * * * *